_United States Patent_ [19]

Donald et al.

[11] Patent Number: 4,681,966

[45] Date of Patent: Jul. 21, 1987

[54] INTERMEDIATE FOR THIOL BASED COLLAGENASE INHIBITORS

[75] Inventors: David K. Donald, High Wycombe; Michael M. Hann, Watlington; John Saunders, Ickford; Harry J. Wadsworth, High Wycombe, all of Great Britain

[73] Assignee: G. D. Searle & Co., Chicago, Ill.

[21] Appl. No.: 847,367

[22] Filed: Apr. 2, 1986

Related U.S. Application Data

[63] Continuation of Ser. No. 703,973, Feb. 21, 1985, which is a continuation-in-part of Ser. No. 685,180, Dec. 21, 1984.

[51] Int. Cl.[4] ............... C07C 153/023; C07C 153/017
[52] U.S. Cl. .................... 558/255; 564/154
[58] Field of Search ........................ 558/255

[56] References Cited

U.S. PATENT DOCUMENTS 4,411,836 10/1983 Ohashi et al. .................... 558/255

*Primary Examiner*—Henry R. Jiles
*Assistant Examiner*—Robert C. Whittenbaugh
*Attorney, Agent, or Firm*—Mary Jo Kanady; Paul D. Matukaitis

[57] ABSTRACT

This invention relates to compounds of the formula

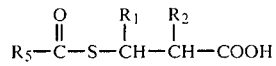

wherein $R_1$ represents lower alkyl, phenyl, or phenyl lower alkyl; $R_2$ represents lower alkyl; and $R_5$ represents lower alkyl. These compounds are useful as intermediates in the preparation of collagenase inhibiting compounds which are useful in the treatment of arthritis and are of the formula

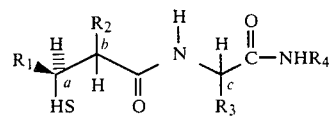

wherein $R_1$ represents lower alkyl, phenyl or phenyl lower alkyl; $R_2$ and $R_4$ represent lower alkyl; and $R_3$ represents lower alkyl, benzyloxyalkyl, alkoxybenzyl or benzyloxybenzyl wherein the oxyalkyl or alkoxy moiety contain 1 to 6 carbon atoms; and a, b, and c represent chiral centers with optional R or S stereochemistry.

1 Claim, No Drawings

INTERMEDIATE FOR THIOL BASED COLLAGENASE INHIBITORS

This is a continuation of application Ser. No. 06/703,973, filed Feb. 21, 1985, which is a continuation-in-part of Ser. No. 06/685,180 filed Dec. 21, 1984.

BACKGROUND OF THE INVENTION

The prior art extensively discloses methylenethiol type collagensase inhibitors:
  i. Biochem. Biophys. Res. Commun. 101, 1251 (1981).
  ii U.S. Pat. Nos. 4,374,765, 4,371,465, 4,235,885, 4,297,275, 4,327,111, 4,382,081, 4,242,354.
  iii Gt. Brit. 2,092,574, Gt. Brit. 2,090,591.

It has been discovered that modification of the structure of the prior art compounds by introduction of a substituent on the methylenethiol carbon so that the thiol moiety is adjacent an assymetric center surprisingly increases the ability of the compounds of the prior art or related to the prior art to inhibit collagenase.

For example, the ability of the prior art compounds described as A, B, and C below to inhibit mammalian collagenase is greatly increased by changing $$HS-CH_2- \text{ to } HS-\underset{\underset{|}{|}}{\overset{\overset{CH_3}{|}}{C}}-$$

i.e. forming an assymetric center adjacent the thiol in accordance with the present invention.

More specifically, compounds of the following formulae A, B, and C are so modified.

$$R-S-CH_2-\underset{\underset{R_1}{|}}{CH}-\overset{\overset{O}{\|}}{C}-(AA_n)_p-NH(CH_2)_m-CHR_2R_3 \quad (A)$$

or salts thereof, wherein
R is hydrogen, alkanoyl of 2 to 10 carbon atoms or arylcarbonyl;
$R_1$ is lower alkyl of 1 to 10, preferably 1 to 6, carbon atoms, cycloalkyl of 3 to 7 carbon atoms, aryl or arylalkyl;
$R_2$ is hydrogen, $$-\text{lower alkyl-}\overset{\overset{O}{\|}}{C}NH_2 \text{ or } -\text{lower alkyl-}NH\overset{\overset{O}{\|}}{C}NH_2;$$

$$R_3 \text{ is } -\overset{\overset{O}{\|}}{C}-O-R_4, -\overset{\overset{O}{\|}}{C}NH_2, -C\equiv N, -\underset{\underset{H}{|}}{C}=O, -\underset{\underset{H}{|}}{\overset{\overset{R_5}{|}}{C}}-R_6,$$

$$-\underset{\underset{R_8}{|}}{N}-R_7, -OR_9, -Cl, -Br \text{ or } -NH\overset{\overset{NH}{\|}}{C}-NH_2;$$

$R_4$ is hydrogen, methyl, ethyl, or $$-CH_2-\bigcirc$$

$R_5$ and $R_6$ are each independently selected as $-OCH_3$ or $-OCH_2CH_3$ or are combined as $-OCH_2CH_2O-$ or $-O-(CH_2)-O-$;

$R_7$ and $R_8$ are each independently selected as hydrogen, methyl or ethyl or are combined as $-(CH_2)_4-$; $-(CH_2)_5-$ or $-CH_2CH_2-O-CH_2CH_2-$;

$R_9$ is hydrogen, methyl, ethyl $$-\overset{\overset{O}{\|}}{C}-CH_3 \text{ or } -\overset{\overset{O}{\|}}{C}-\bigcirc$$

m is an integer from 0 to 7;
p is an integer from 1 to 3;
$AA_n$ is an amino acid chain of from one to three amino acids;
n is 1 or 1, 2 or 1, 2, 3;
when p is 1, $AA_n$ is $AA_1$;
when p is 2, $AA_n$ is $AA_1$-$AA_2$;
when p is 3, $AA_n$ is $AA_1$-$AA_2$-$AA_3$;
$AA_1$ is glycine or alanine;
$AA_2$ is glycine or alanine;
$AA_3$ is leucine, glutamine or isoleucine.
Likewise compounds of formula B $$R_1-S-CH_2-\underset{\underset{R_3}{|}}{CH}-\overset{\overset{O}{\|}}{C}-NH-(CH_2)_n-R_2 \quad (B)$$

or a salt thereof, wherein
$R_1$ is hydrogen, alkanoyl or 2 to 10 carbon atoms, or arylcarbonyl;

$$R_2 \text{ is } -NH-\overset{\overset{NH}{\|}}{C}-NH_2, -\overset{\overset{O}{\|}}{C}-R_4$$

$$-\underset{\underset{R_4}{|}}{C}-(O-alkyl)_2, \text{ OR } -\underset{\underset{O}{\diagdown}}{\overset{\overset{R_4}{|}}{\underset{}{C}}}\overset{O}{\diagup}$$

wherein $R_4$ is hydrogen, alkyl or aryl;
$R_3$ is alkyl of 3 to 8 carbon atoms, cycloalkyl of 3 to 7 carbon atoms, aryl or arylalkyl; and n is an integer of 1 to 20.

Also compounds of formula C.

$$R_1-S-CH_2-\underset{\underset{CH_2CH(CH_3)_2}{|}}{CH}-\overset{\overset{}{\underset{\underset{O}{\|}}{C}}}{-}R_2 \quad (C)$$

and salts thereof, wherein
$R_1$ is hydrogen or alkanoyl of 2 to 10 carbon atoms;
$R_2$ is hydroxy, amino, or $$-ONH-(CH_2)_m-\underset{\underset{R_3}{|}}{CH}-\overset{\overset{O}{\|}}{C}-R_4$$

$R_3$ is hydrogen, alkyl of 1 to 4 carbon atoms.

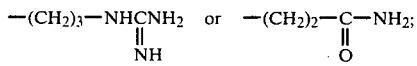

$R_4$ is hydroxy, amino, arginine, leucine, glutamine, alanine or glycine; and m is 0 or an integer of 1 to 9.

This invention relates to the above-described novel compounds having pharmacological activity, to the production thereof, to compositions containing them, and to their use in the treatment of management of conditions or diseases, e.g., rheumatoid arthritis, in which collagenase promoted collagen breakdown is a causative factor.

The compounds of the invention act as inhibitors of mammalian collagenase which initiates collagen breakdown. Extensive proteolytic enzyme promoted degradation of articular cartilage is associated with joint destruction in rheumatoid arthritis. Collagen is one of the major components of the protein matrix of joint cartilage and bone. Histological observations of rheumatoid lesions have established that such lesions are characterized by the proliferation of synovial lining cells with subsequent neovascularization and infiltration by lymphocytes, macrophages and plasma cells, collectively referred to as soft tissue or "pannus". The importance of such soft tissue in cartilage erosion has been well demonstrated.

Evanson and coworkers, for example, found that large amounts of neutral collagenase are produced by pannus tissue (Evanson, J. M., et al., Arthritis & Rheum., 27, 2639–2651, 1968). More recently, others have confirmed that neutral collagenase plays an important degradative role in the arthritic joints of experimental animals (see Cambray, et al., Rheumatol Int. 1, 11–16 and 17–20, 1981) and in humans (Cawston, et al., Arthritis & Rheum., 27, 285–290, 1984).

A mono-specific antiserum to purified synovial collagenase has been used to localize the enzyme in rheumatoid tissues (Wolley, et al., Eur. J. Biochem., 69, 421–428, 1976). Immunoreactive collagenase was detected in high density at the cartilage-pannus junction (Wooley, et al., Arthritis & Rheumatism, 20, 1231–1349.) Wooley, et al., (Science, 200, 773–775, 1978) have further identified a sub-population of synovial cells responsible for collagenase production.

Thus, the foregoing observations have provided conclusive evidence that collagenase is directly involved in the cartilage erosion process seen in rheumatoid arthritis. Accordingly, the compounds of the present invention which specifically inhibit mammalian collagenase are pharmacologically useful in the treatment of rheumatoid arthritis and related diseases in which collagenolytic activity is a contributing factor, such as corneal ulceration, peridontal disease, tumor invasion, dystrophic epidermolysis bullosa, etc.

These compounds have substantially no angiotensin converting enzyme (ACE)-inhibiting activity. ACE inhibitors are described in European Appl. No. A-0012401. ACE is a carboxydipeptidase—it cleaves a peptide substrate two residues from the C-terminus. Consequently the C-terminal carboxylic acid is a prime recognition site for both substrate and inhibitors; removal of this group drastically reduces inhibitory potency. Collagenase, on the other hand, is an endopeptidase and, as such, has no prerequisite for this binding interaction. Additionally, the structure of collagen differs essentially from angiotensin-I which is a decapeptide and is cleaved at a phenylalanine-histidine bond to give an octapeptide (angiotensin-II and a dipeptide (histidylleucine). Collagen is much more complex, in being a triple helix, each strand of the helix containing of the order of 1,000 amino acid residues, the sequence of amino acids around the site cleaved by collagenase being completely different from that around the cleavage site of Angiotensin I. Collagenase cleaves approximately two-thirds of the way along the chain from the N-terminus. The amide bond which is cleaved by collagenase is either a glycine-leucine or a glycine-isoleucine bond.

For use in the treatment of rheumatoid arthritis or other collagen based degradative diseases, the compounds of this invention may be administered to a mammal in need thereof orally or by injection. The daily total effective dose will generally range between 25 mg. to 750 mg.

The compounds of this invention can be formulated in compositions such as tablets, capsules or elixirs for oral administration or in sterile solutions or suspensions for parenteral administration. About 10 mg., for example, of a compound according to the invention is compounded with a physiologically acceptable vehicle, carrier, excipient, binder, preservative, stabilizer, flavour, etc., in a unit dosage form as called for by accepted pharmaceutical practice. (See for example, Remington's Pharmaceutical Science Mach Publishing Co., Easton, Pa. 1965). The amount of active substance in these compositions or preparations is such that a suitable dosage in the range indicated is obtained.

The compounds according to the invention may be made by methods which are generally known in peptide chemistry for analogous compounds. In particular it is to be understood that reactive groups not involved in a particular reaction (e.g. amino, carboxy, hydroxy etc.,) may be protected by methods standard in peptide chemistry prior to reactions of other groups and subsequently deprotected.

The intermediates of use in the production of the end-products are either known compounds or can be made by known methods, as described in the Examples.

DETAILED DESCRIPTION OF THE INVENTION

This invention encompasses compounds of the formula

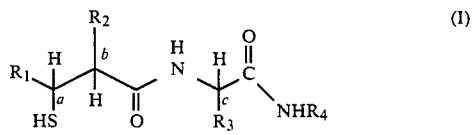

(I)

wherein $R_1$ represents lower alkyl, phenyl or phenyl lower alkyl;

$R_2$ and $R_4$ represent lower alkyl; and $R_3$ represents lower alkyl, benzyloxyalkyl alkoxybenzyl or benzyloxybenzyl wherein the oxyalkyl or alkoxy moiety contain 1 to 6 carbon atoms; and a, b, and c represent chiral centers with optional R or S stereochemistry.

A preferred embodiment is a compound of the formula

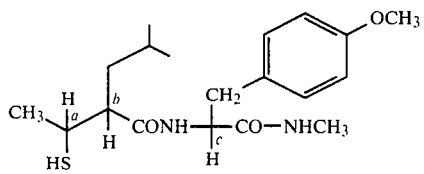

and particularly the isomers thereof having NMR spectral peaks at:

[δ(CDCl₃] 0.86 (6H, d, J=5 Hz, (CH₃)₂CH); 1.2 (3H, d, J=6 Hz, CH₃CHSH); 1.54 (3H, m, CHCH₂); 2.2 (1H, m, CHCO); 2.72 (3H, d, J=4 Hz NHCH₃); 3.02 (3H, m, CH₂C₆H₄, CHSH); 3.78 (3H, s, CH₃7.0); 4.6 (1H, q, J=5 Hz NHCHCO); 5.9 (1H, s, HN); 6.4 (1H, d, J=7 Hz, NH) 6.78 and 7.10 (4H, each d, each J=9 Hz, (C₆H₄).

and those as follows:

[δ(CDCl₃)] 0.78 (6H,m,(CH₃)₂CH); 1.28 (3H, d, J=5 Hz, CH₃CHSH); 1.16 (3H, m, CH CH₂); 2.16 (1H, m, CHCO); 2.74 (3H, d, J−5 HZ, CH₃NH); 3.02 (3H, m, CHSH,CH₂C₆H₄) 3.76 (3H, s, CH₃O); 4.68 (1H, m, NHCHCO); 6.3 (1H, m, NH); 6.52 (1H, m, NH); 6.78 and 7.08 (4H, each d, each J=8 Hz, C₆H₄).

Those compounds having the S configuration of the c chiral center are particularly preferred.

Other preferred embodiments of the invention are compounds of the formulae

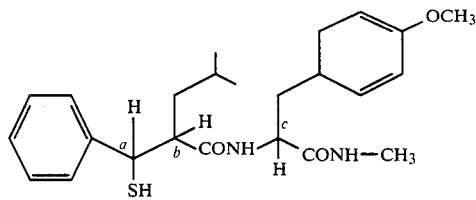

and

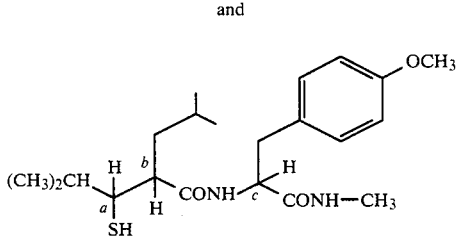

and

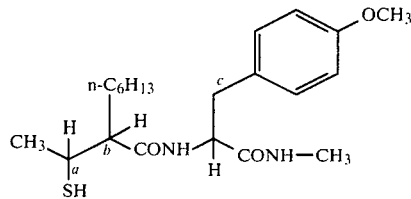

and

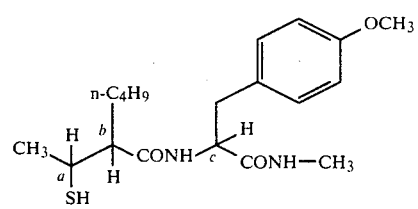

and

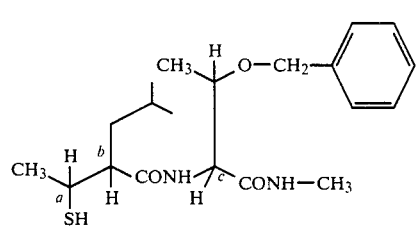

as well as

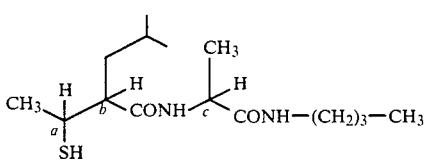

encompassing the respective diastereomers or pairs thereof for the two chiral centers at a, b; the preferred stereochemistry of the chiral center "c" is the S-configuration.

As used herein, "lower alkyl" refers to a straight or branched chain alkyls having 1 to 6 carbon atoms, and to cycloalkyls having 3 to 7 carbon atoms.

Alkoxy refers to alkoxy groups having a lower alkyl group as defined above.

Compounds of this invention are prepared according to the following reaction Scheme

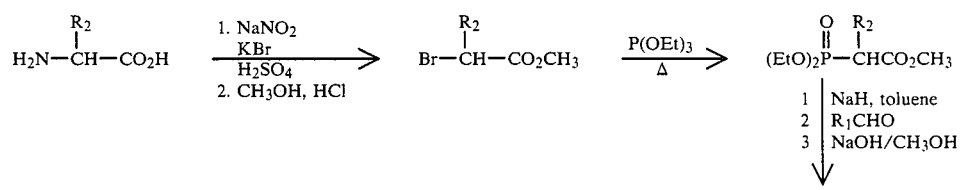

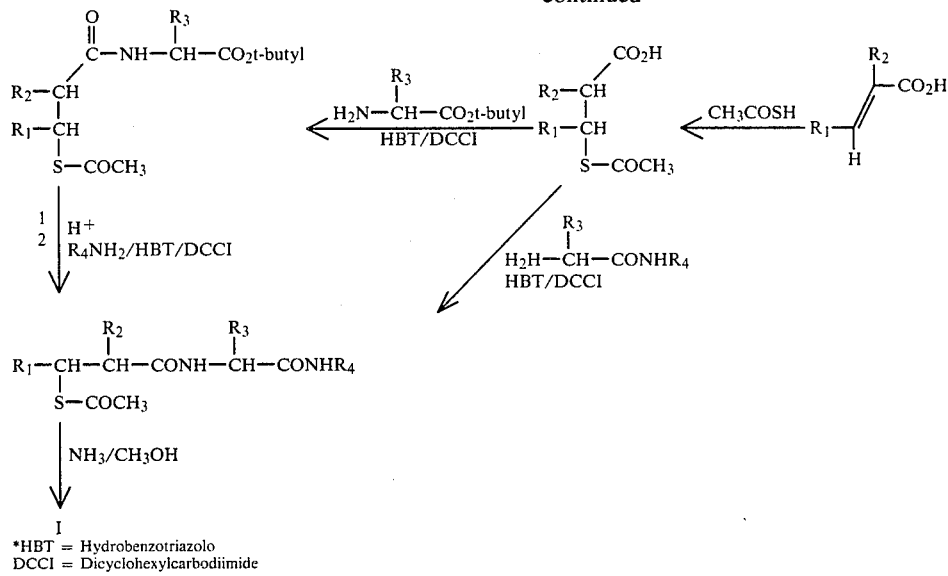

*HBT = Hydrobenzotriazolo
DCCI = Dicyclohexylcarbodiimide

Compounds of this invention are advantageously prepared by a diastereoselective route which affords only two of the potential four diastereisomers according to the following scheme utilizing asymmetric induction.

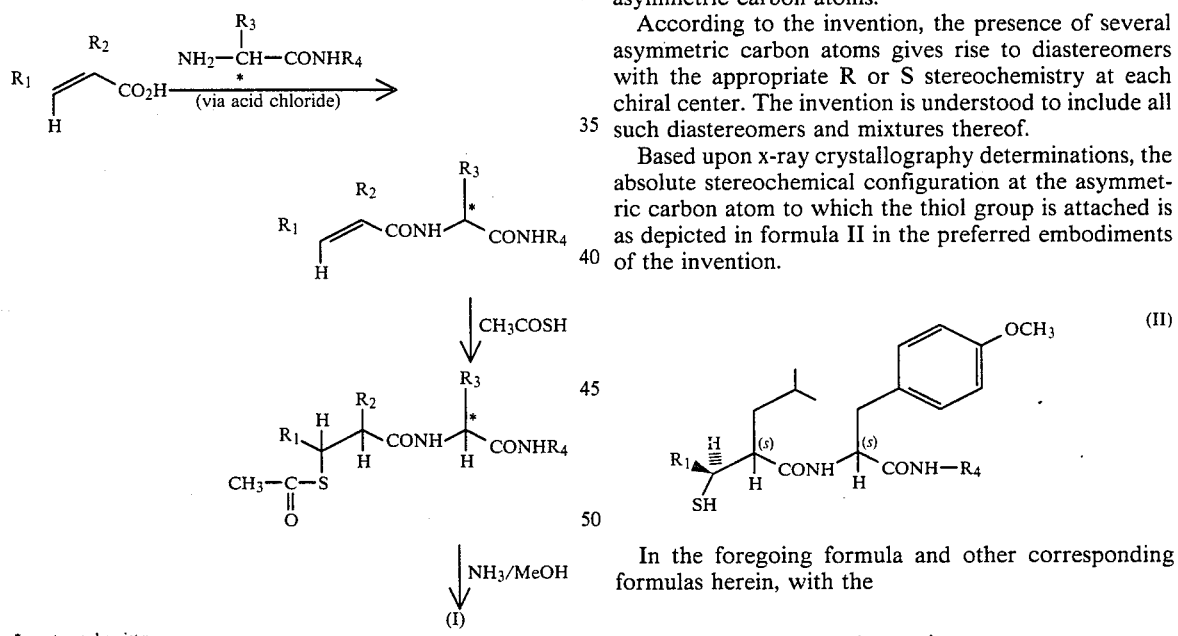

\* = stereochemistry $R_1$, $R_2$, $R_3$, and $R_4$ are as previously defined. Thus the compound

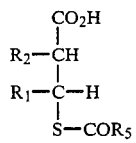

where $R_1$ and $R_2$ are defined above and $R_5$ is lower alkyl is a key intermediate in preparing compounds of this invention as well as converting prior art compounds to compounds having an asymmetric center adjacent the thiol.

There are several chiral centers in the compounds according to the invention because of the presence of asymmetric carbon atoms.

According to the invention, the presence of several asymmetric carbon atoms gives rise to diastereomers with the appropriate R or S stereochemistry at each chiral center. The invention is understood to include all such diastereomers and mixtures thereof.

Based upon x-ray crystallography determinations, the absolute stereochemical configuration at the asymmetric carbon atom to which the thiol group is attached is as depicted in formula II in the preferred embodiments of the invention.

In the foregoing formula and other corresponding formulas herein, with the portion of the molecule substantially in the plane of the page, the symbol (=) means the hydrogen atom is behind the plane of the page and the symbol (◄) means the $R_1$ group is in front of the plane of the page.

It will be appreciated by those skilled in the art that the designation of the three asymmetric centers shown as R,S,S or S,S,S according to the Cahn-Ingold-Prelog convention is specifically dependent upon the nature of the $R_1$ substituent. Thus, for example, when $R_1$ is methyl, the stereochemistry will be denoted (S), whereas when $R_1$ is phenyl, the configuration is (R).

However, irrespective of the (R,S) convention for designation of the stereochemistry, the absolute configuration remains unchanged and will be as shown in formula II.

TABLE 1 below illustrates the structures of the compounds in the examples.

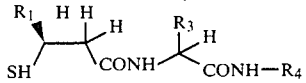

| Example No. | $R_1$ | $R_2$ | $R_3$ | $R_4$ |
|---|---|---|---|---|
| 1 | $-CH_3$ | $-CH_2CH(CH_3)_2$ | $-CH_2-C_6H_4-OCH_3$ | $-CH_3$ |
| 2 | $-C_6H_5$ | $-CH_2CH(CH_3)_2$ | $-CH_2-C_6H_4-OCH_3$ | $-CH_3$ |
| 3 | $-CH(CH_3)_2$ | $-CH_2CH(CH_3)_2$ | $-CH_2-C_6H_4-OCH_3$ | $-CH_3$ |
| 4 | $-CH_3$ | $-(CH_2)_5CH_3$ | $-CH_2-C_6H_4-OCH_3$ | $-CH_3$ |
| 5 | $-CH_3$ | $-(CH_2)_3CH_3$ | $-CH_2-C_6H_4-OCH_3$ | $-CH_3$ |
| 6 | $-CH_3$ | $-CH_2CH(CH_3)_2$ | $-CH(CH_3)OCH_2C_6H_5$ | $-CH_3$ |
| 7 | $-CH_3$ | $-CH_2CH(CH_3)_2$ | $-CH_3$ | $-(CH_2)_3CH_3$ |
| 8 | $-CH_3$ | $-CH_2-CH(CH_3)_2$ | $-CH_2-C_6H_4-O-CH_3$ | $-CH_3$ |

TABLE 2 illustrates the stereochemical specificity for collagenase inhibition.

| Example No. | Isomer | $IC_{50}$ ($\mu M$) Human Rheumatoid Synovial collagenase |
|---|---|---|
| 1 | A1 | 19. |
| 1 | A2 | 13. |
| 1 | B1 | 0.22 |
| 1 | B2 | 1.5 |
| 2 | A1 | 0.27 |
| 2 | A2 | 1.71 |
| 2 | B1 | 3.9 |
| 2 | B2 | 12.0 |
| 3 | A | 2 |
| 3 | B | 5 |
| 4 | A | 5 |
| 4 | B | 140 |
| 5 | A | 0.2 |
| 5 | B | 1.0 |
| 6 | A | 0.45 |
| 6 | B | 4.9 |
| 7 | A | 4.9 |
| 7 | B | 2.0 |
| 7 | C | 1.2 |

The compounds according to the invention exhibit inhibitor action against collagenase. This was determined following the procedure of Cawston and Barrett, Anal. Biochem,. 99, 340-345 (1979) whereby the 1 mM of the inhibitor being tested or dilutions thereof are incubated at 37° C. for 16 hours with native collagen and collagenase (buffered with Tris HCl—CaCl$_2$; pH 7.6). The collagen is acetyl $^{14}$C collagen. The samples are centrifuged to sediment undigested collagen and an aliquot of the radiactive supernatant removed for assay on a scintillation counter as a measure of hydrolysis. The collagenase activity in the presence of 1 mM inhibitor, or a dilution thereof, is compared to activity in a control devoid of inhibitor and the results reported as that inhibitor concentration effecting 50% inhibition of the collagenase. Table II illustrates the activity of compounds of this invention.

For use in treatment of rheumatoid arthritis the compounds of this invention can be administered by any convenient route preferably in the form of a pharmaceutical composition adapted to such route and in a dose effective for the intended treatment. In the treatment of arthritis administration may conveniently be by the oral route or by injection intraarticularly into the affected joint. The daily dosage for a 70 kilogram mammal will be in the range of 10 milligrams to 1 gram.

The compounds according to the invention exhibit inhibitory action against collagenase. This was determined following the procedure of Cawston and Barrett, Anal. Biochem., 99, 340-345 (1979) whereby the 1 mM of the inhibitor being tested or dilutions thereof are

TABLE 3[1]

illustrates the increased activity resulting from forming an asymmetric center adjacent to the thiol.

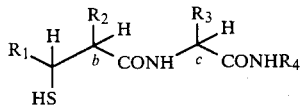

| $R_1$ | $R_2$ | $R_3$ | $R_4$ | Example | Isomer | $IC_{50}$[2] |
|---|---|---|---|---|---|---|
| $-H$ | $CH_2-CH(CH_3)_2$ | $-CH_2-C_6H_4-4-OCH_3$ | $-CH_3$ | — | R + S[3] | 3.6 $\mu M$ |
| $-CH_3$ | $CH_2-CH(CH_3)_2$ | $-CH_2-C_6H_4-4-OCH_3$ | $-CH_3$ | 1 | B1 isomer | 0.22 $\mu M$ |
| $-H$ | $CH_2-CH(CH_3)_2$ | $-CH(CH_3)O-CH_2C_6H_5$ | $-CH_3$ | — | R + S[3] | 4.8 $\mu M$ |
| $-CH_3$ | $CH_2-CH(CH_3)_2$ | $-CH(CH_3)O-CH_2C_6H_5$ | $-CH_3$ | 6 | pair A of diastereomers | 0.45 $\mu M$ |
| $-H$ | $-CH_2-CH(CH_3)_2$ | $-CH_3$ | $-(CH_2)_3CH_3$ | — | R + S[3] | 37 $\mu M$[4] |
| $-CH_3$ | $-CH_2-CH(CH_3)_2$ | $-CH_3$ | $-(CH_2)_3-CH_3$ | 7 | single isomer | 1.2 $\mu M$ |

FOOTNOTES
[1]all compounds in table 3 have S—stereochemistry at c
[2]against human rheumatoid sinovial collagenase
[3]mixture of diastereomers at b
[4]mean of two results; individual results are 25 $\mu M$ and 44 $\mu M$ respectively.

The compounds according to the invention exhibit inhibitor action against collagenase. This was determined following the procedure of Cawston and Barrett, Anal. Biochem,. 99, 340-345 (1979) whereby the 1 mM incubated at 37° C. for 16 hours with native collagen and collagenase (buffered with Tris HCl—CaCl$_2$; pH 7.6). The collagen is acetyl $^{14}$D collagen. The samples are centrifuged to sediment undigested collagen and an aliquot of the radioactive supernatant removed for assay on a scintillation counter as a measure of hydrolysis. The collagenase activity in the presence of 1 mM inhibitor, or a dilution thereof, is compared to activity in a control devoid of inhibitor and the results reported as that inhibitor concentration effecting 50% inhibition of the collagenase. Table II illustrates the activity of compounds of this invention.

For use in treatment of rheumatoid arthritis the compounds of this invention can be administered by any convenient route preferable in the form of a pharmaceutical composition adapted to such route and in a dose for the intended treatment. In the treatment of arthritis administration may conveniently be by the oral route or by injection intra-articularly into the affected joint. The daily dosage for a 70 kilogram mammal will be in the range of 10 milligrams to 1 gram.

In order that the invention may be more fully understood, the following specific examples are given without limiting the scope of the invention thereto.

EXAMPLE 1

N-[2-(1-Mercaptoethyl)-4-methylpentanoyl]-O-methyl-L-tyrosine N-Methylamide (a) 4-Methyl-2-(diethylphosphono)pentanoic acid methyl ester 2-Bromo-4-methyl-pentanoic acid methyl ester (193 g, 0.92M) and triethyl phosphite (330 ml, 1.84M) were heated to 150° C. The reaction temperature was increased to 200° C. over 6 h and a distillate b.p. 37°–60° C. (80 g) collected with an air condenser. The residue was distilled under high vacuum to afford 2 fractions (a) mainly triethyl phosphite b.p. 40°–80° C. at 0.4 mm Hg and (b) 4-methyl-2-(diethyl phosphono)pentanoic acid methyl ester (188 g) b.p. 96°–100° C. at 0.4 mm Hg (Found: C, 47.6; H,8.6.$C_{11}H_{23}O_5P+0.6H_2O$ requires C, 47.7; H, 8.8%); $\delta(CDCl_3)$ 0.9 (6H, dd,J=7 Hz, J=7 Hz, $(CH_3)_2C$); 1.04–2.10 (3H, m, $CH_2CH$); 1.34 (6H, t, J=7 Hz, $(CH_2CH_3)_2$); 3.09 (1H, ddd, J=23 Hz, J=10 Hz, J=4 Hz, $\underline{CH}P$); 3.73 (3H, s, $CH_3O$); 4.14 (4H, m, $(\underline{CH_2}CH_3)_2$).

(b) E and Z 2-(2-Methylpropyl)-but-2-enoic Acid methyl ester

4-Methyl-2-(diethylphosphono)pentanoic acid methyl ester (188 g, 0.7 mol) in dry toluene (800 ml) was treated at 20° with sodium hydride (23.1 g of an 80% suspension in oil, 0.77M) under an atmosphere of nitrogen. The mixture was heated under reflux for 40 min., cooled to room temperature and acetaldehyde (46.3 g, 1.05M) added over 10 minutes. After 16 h at room temperature the mixture was partitioned between water and ether and the aqueous layer extracted with fresh ether. The combined organic extracts were washed with aqueous saturated sodium hydrogen carbonate solution, dried and evaporated in vacuo. Fractional distillation of the resulting oil under reduced pressure gave the required methyl ester (39.2 g) as a mixture of E and Z isomers, b.p. 40° at 0.5 mmHg $\delta(CDCl_3)$. 0.88, (6H, m, $(CH_3)_2C$); 1.3 (1H, m, CH), 1.8 and 1.96 (3H, each d, each J=7 Hz, $CH_3$—); 2.12 and 2.22 (2H, each d, each J=7 Hz, $CH_2$); 3.72 and 3.74 (3H, s, $CH_3O$); 5.94 and 6.9 (1H, each q, each J=8 Hz $C\underline{H}CH_3$).

(c) E and Z-2-(2-Methylpropyl)-but-2-enoic Acid

E and Z-2-(2-Methylpropyl)-but-2-enoic acid methyl ester (10 g) in ethanol (200 ml) was treated with potassium hydroxide (20 g) in water (10 ml) under reflux for 5 h. The reaction was concentrated in vacuo to an oil which was partitioned between water and dichloromethane. The aqueous layer was acidified with hydrochloric acid (6M) and extracted with dichloromethane. The organic extract was dried over sodium sulphate and concentrated in vacuo to afford a mixture of E and Z-2-(2-methylpropyl)-but-2-enoic acid (6.5 g) as an oil (Found: C, 64.7; H, 9.4. $C_8H_{14}O_2+0.3H_2O$ requires: C, 65.0; H, 9.9%); $\delta(CDCl_3)$ 0.9 (6H, d, J=7 Hz, $(CH_3)_2C$); 1.82 (1H, m, CH); 1.84 and 2.06 (3H, each d, each J=6 Hz, $CH_3CH$); 2.12 and 2.2 (2H, each d, each J=6 Hz, $CH_2C$); 6.1 and 7.06 (1H, each q, each J=7 Hz, CH).

(d) 2-(RS)-(1-(RS)-S-Acetylmercaptoethyl)-4-methylpentanoic Acid

E and Z-2-(methylpropyl)-but-2-enoic acid (1 g) was treated with thioacetic acid (5 ml) for 72 h at reflux temperature. The residue after evaporation of the excess thioacetic acid was taken into dichloromethane and the solution extracted with aqueous saturated sodium hydrogen carbonate solution. The aqueous phase was acidified with dilute hydrochloric acid and extracted with dichloromethane followed by evaporation of the organic extracts to afford the required acid (0.85 g) as a gum. (Found: C, 52.4; H, 8.2; $C_{10}H_{18}O_3S+0.6H_2O$ requires: C, 52.4; H, 8.4%) $\delta(CDCl_3)$. 0.92 (6H, m $(CH_3)_2CH$) 1.38 (3H, d, J=6 Hz, $CH_3CHS$); 1.66 (3H, m, $CH_2CH$); 2.34 (3H, s, $CH_3COS$); 2.68 (1H, m,CHCO); 3.8 (1H, m, CHS).

(e) t-Butyl N-[2-(1-S-Acetylmercaptoethyl)-4-methylpentanoyl]-O-methyl-L-tyrosine t-Butylester The foregoing acid (2.63 g) stirred at 0° in dichloromethane (20 ml) was treated with 1-hydroxybenzotriazole (1.81 g) and N,N'-dicyclohexylcarbodiimide (2.30 g) followed by O-methyl-L-tyrosine t-butyl ester (2.45 g) and then allowed to warm to 20° over 2 h. After 24 h at 20° the mixture was filtered and the filtrates washed in turn with aqueous saturated sodium hydrogen carbonate solution, water and aqueous citric acid (3N) and then dried over sodium sulphate. The gum isolated from the dichloromethane was chromatographed on silica in 40% ether in hexane to afford the desired peptide as a mixture of two pairs of diastereoisomers. The faster running pair ("PAIR A", 1.1 g) was obtained as an oil which solidified on standing m.p. 70°–75° C. (Found: C, 61.0; H, 7.2; N, 4.4. $C_{24}H_{37}N_1O_5S+H_2O$ requires: C, 61.4; H, 8.4; N, 2.0%); $\delta(CDCl_3)$ 0.88 (6H, m, $(CH_3)_2C$); 1.16 and 1.26 (3H, each d, each J=6 Hz, $CH_3CHS$); 0.98 to 1.68 (3H, m, $CHCH_2$); 1.44 (9H, s, $(C\underline{H_3})_3C$); 2.32 (3H, s, $CH_3COS$); 2.44 (1H, m, CHCO); 3.06 (2H, m, $CH_2C_6H_4$); 3.6 (1H, m, CHS); 3.78 (3H, s, $CH_3O$); 4.76 (1$\overline{H}$, m, $NHCHCO$); 6.16 (1H, m, NH); 6.78 and 6.8, 7.09 and 7.12 (4$\overline{H}$, each d, each J=8 Hz, $C_6H_4$).

The slower running pair ("PAIR B", 1.3 g) crystallised from ether as needles m.p. 100°–103° C. (Found: C, 61.3; H, 7.8; N, 3.0 $C_{24}H_{37}N_1O_5S+H_2O$ requires: C, 61.4; H, 8.4; N, 3.0%); $\delta(CDCl_3)$ 0.84 (6H, m, $(CH_3)_2CH$); 1.24 and 1.3 (3H, each d, each J=6 Hz, $C\underline{H_3}CHSH$); 1.42 and 1.44, (9H, each s, $(CH_3)_3C$); 1.34 to 1.68 (3H, m, $CHCH_2$); 2.3 (3H, s, $CH_3COS$); 2.3 (1H, m, CHCO); 3.02 (2$\overline{H}$, m, $CH_2C_6H_4$); 3.62 (1H, m, CHS); 3.62 (3H, s, $CH_3O$); 4.76 (1$\overline{H}$, m, $NHC\underline{H}CO$); 5.92 (1H, m, NH); 6.78 and 6.79, 7.08 and 7.12 (4H, each d, each J=8 Hz, C$_6$H$_4$).

(f) N-[2-(1-S-Acetylmercaptoethyl)-4-methylpentanoyl]-O-methyl-L-tyrosine N-Methylamide The faster-running pair of isomers ("PAIR A") of the foregoing S-acetyl compound (400 mg) was treated at 20° with TFA (10 ml) and water (0.5 ml) for 3 h. The solvents were evaporated in vacuo and re-evaporated after the addition of toluene. To the residue in dichloromethane (10 ml) stirred at 0° was added 1-hydroxybenzotriazole (133 mg) and N-ethyl-N'-(3-dimethylaminopropyl)carbodiimide hydrochloride (180 mg) followed by methylamine hydrochloride (80 mg). The pH was adjusted to 7 with N-methylmorpholine and the mixture stored at 20° for 16 h. The mixture was then diluted with dichloromethane and washed successively with aqueous saturated sodium hydrogen carbonate, water and finally aqueous citric acid (3M). The material isolated from the dichloromethane was purified by chromatography on silica in an increasing gradient of ethyl acetate in hexane to yield two separated diastereoisomers of N-[2-(1-S-Acetylmercaptoethyl)-4-methylpentanoyl]-O-methyl-L-tyrosine N-methylamide. The faster running isomer (A1, Rf=0.39 in 1:1 ethyl acetate dichloromethane; 90 mg) crystallised from ether as needles, m.p. 78°-80°; (Found: C, 61.4; H, 8.1; N, 6.7. C$_{21}$H$_{32}$N$_2$O$_4$S requires: C, 61.7; H, 7.9; N, 6.8%); δ(CHCl$_3$) 0.78 (6H, s, (CH$_3$)$_2$CH); 1.26 (3H, d, J=5 Hz, CH$_3$CHS); 1.1-1.68 (3H, m, CHCH$_2$); 2.3 (3H, s, CH$_3$COS); 2.54 (1H, m, CHCO); 2.74 (3H, d, J=4 Hz CH$_3$NH); 2.9 and 3.02 (each 1H, each d, J=15 Hz, J=8 Hz, CH$_2$C$_6$H$_4$); 3.66 (1H, t, J=5 Hz, CHSH); 3.74 (3H, s, CH$_3$O); 4.84 (1H, q, J=6 Hz, NHCHCO); 6.92 (2H, m, 2×NH); 6.74 and 7.06 4H, each d, each J=8 Hz, C$_6$H$_4$). Isomer A2 (Rf=0.33 in 1:1 ethyl acetate dichloromethane; 110 mg) was obtained as a white solid, m.p. 70°-72°; (Found: C, 61.0; H, 7.9; N, 6.7. C$_{21}$H$_{32}$N$_2$O$_4$S+0.3 H$_2$O requires: C, 60.9; H, 7.9; N, 6.8%); δ(CDCl$_3$) 0.76 (6H, d, J=6 Hz (CH$_3$)$_2$CH); 1.41 (2H, m, CH$_2$); 1.24 (3H, d, J=CH$_3$CHS); 1.62 (1H, m, CH(CH$_3$)$_2$); 2.3 (3H, s, CH$_3$COS) 2.4 (1H, m, CHCO); 2.78 (3H, d, J=4 Hz, CH$_3$NH); 2.94 and 3.08 (2H, each dd, each J=12 Hz, J=7 Hz, CH$_2$C$_6$H$_4$); 3.62 (1H, dq, J=7 Hz, J=7 Hz, CHS); 3.74 (3H, s, CH$_3$O); 4.82 (1H, q, J=Hz, NHCHCO); 6.72 and 7.06 (4H, each d, each J=8 Hz, C$_6$H$_4$); 6.88 (1H, m, HN); 7.0 (1H, m, NH).

In an exactly analogous way single isomers B1 and B2 were prepared from "PAIR B" of N-[2-(1-S-acetylmercaptoethyl)-4-methylpentanoyl]-O-methyl-L-tyrosine-t-butyl ester.

Isomer B1 of N-[2-(1-S-acetylmercaptoethyl)-4-methyl-pentanoyl]-O-methyl-L-tyrosine N-methylamide (Rf=0.45 in 1:1 ethyl acetate dichloromethane, crystallised from ether as needles, m.p. 84°-85°; (Found: C, 61.8; H, 8.1; N, 6.6. C$_{21}$H$_{32}$N$_2$O$_4$S requires: C, 61.7; H, 7.9; N, 6.9%); δ(CDCl$_3$) 0.86 (6H, d, J=6 Hz, (CH$_3$)$_2$CH); 1.2 (3H, d, J=6 Hz, CH$_3$CHSH); 1.26-1.78 (3H, m, CH$_2$CH); 2.3 (3H, s, CH$_3$CO); 2.36 (1H, m, CHCO); 2.7 (3H, d, J=5 Hz, CH$_3$NH); 2.96 and 3.08 (each 1H, each dd, each J=12 Hz, J=7 Hz, CH$_2$C$_6$H$_4$); 3.66 (1H, dq, J=7 Hz, J=7 Hz, CHSH); 3.78 (3H, s, CH$_3$O); 4.58 (1H, q, J=5 Hz, NHCHCO); 5.8 (1H, m, NH); 6.32 (1H, d, J=6 Hz, NH); 6.8 and 7.2 (4H, each d, each J=8 Hz C$_6$H$_4$).

Isomer B2 (Rf=0.37 in 1:1 ethyl acetate dichloromethane) also crystallised from ether m.p. 140°-155° C. (Found: C, 61.5; H, 7.96; N, 6.8; C$_{21}$H$_{32}$N$_2$O$_4$S requires: C, 61.7; H, 7.9; N, 6.9%); δ(CDCl$_3$) 0.76 and 0.82 (6H, each d, each J=5 Hz (CH$_3$)$_2$CH); 1.2 (3H, m, CH$_2$CH); 1.28 (3H, d, J=6 Hz, CH$_3$CSH); 2.3 (3H, s, CH$_3$CO); 2.32 (1H, m, CHCO); 2.76 (3H, d, CH$_3$NH); 3.04 (2H, m, CH$_2$C$_6$H$_4$); 3.66 (1H, d, q, J=6 Hz, J=6 Hz, CHS); 3.76 (3H, s, CH$_3$O); 4.66 (1H, q, J=6 Hz, NHCHCO); 6.22 (1H, m, NH); 6.36 (1H, d, J=8H, NH); 6.76 and 7.08 (4H, each d, each J=8 Hz, C$_6$H$_4$).

(g) N-[2-(1-Mercaptoethyl)-4-methylpentanoyl]-O-methyl-L-tyrosine N-Methylamide

Each of the four separated diastereoisomers of the foregoing S-acetyl compounds (80 mg) were individually treated under an atmosphere of nitrogen with a saturated solution of ammonia in methanol (5 ml) for 12 h at 20°. Evaporation of the methanol gave a solid which was triturated with hexane to afford the required thiol (60 mg).

Isomer A1 crystallised from ethyl acetate as needles, m.p. 160°-162°; [α]$^{20}$=1.9° (c=0.2, MeOH); (Found: C, 61.1; H, 8.4; N, 7.7; C$_{19}$H$_{30}$N$_2$O$_3$S+0.4H$_2$O requires: C, 61.1; H, 8.3; N, 7.5%); δ(CDCl$_3$) 0.84 (6H, m, (CH$_3$)$_2$CH); 1.28 (3H, d, J=5 Hz, CH$_3$CHSH); 1.22-1.66 (3H, m, CH$_2$CH); 2.26 (1H, m, CHCO); 2.7 (3H, d, J=5 Hz, CH$_3$NH); 3.02 (3H, m, CH$_2$C$_6$H$_4$ CHSH); 3.76 (3H, s, CH$_3$O); 4.62 (1H, q, J=8 Hz, NHCHCO); 6.1 and 6.5 each 1H, each m, 2×NH); 6.8 and 7.12 (4H, each d, each J=8 Hz, C$_6$H$_4$).

Isomer A2 crystallised from ethyl acetate as needles m.p. 120°-130° C.; [α]$^{20}$=1.1 (c=0.2, MeOH); (Found: C, 60.4; H, 8.2; N, 8.0. C$_{19}$H$_{30}$N$_2$O$_3$S+0.6H$_2$O requires: C, 60.5; H, 8.3; N, 7.4%); δ(CDCl$_3$) 0.76 (6H, dd, J=15 Hz and 5 Hz, (CH$_3$)$_2$CH); 1.34 (3H,d,J=6 Hz,CH$_3$CHSH); 1.04-1.66 (3H, m, CHCH$_2$); 2.1 (1H, m, CHCO); 2.76 (3H, d, J=4 Hz, CH$_3$NH); 3.08 (3H, m, CH$_2$C$_6$H$_4$, CHSH); 3.78 (3H, s, OCH$_3$); 4.76 (1H, q, J=6 Hz, NHCHCO); 6.36 (1H, d, J=7 Hz, NH); 6.64 (1H, m, NH) 6.76 and 7.08 (4H each 2H, each d, J=8 Hz, C$_6$H$_4$).

Isomer B1 also crystallised from ethyl acetate as needles m.p. 195°-200° C.; [α]$^{20}$=+14° (C=0.2, MeOH); (Found: C, 61.9; H, 8.4; N, 7.8. C$_{19}$H$_{30}$N$_2$O$_3$S requires: C, 62.3; H, 8.3; N, 7.6%); δ(CDCl$_3$) 0.86 (6H, d, J=5 Hz, (CH$_3$)$_2$CH); 1.2 (3H, d, J=6 Hz, CH$_3$CHSH); 1.54 (3H, m, CHCH$_2$); 2.2 (1H, m, CHCO); 2.72 (3H, d, J=4 Hz NHCH$_3$); 3.02 (3H, m, CH$_3$); 3.02 (3H, m, CH$_2$C$_6$H$_4$, CHSH); 3.62 (3H, s, OCH$_3$); 4.6 (1H, q, J=5 Hz NHCHCO); 5.9 (1H, s, NH); 6.4 (1H, d, J=7 Hz,NH) 6.78 and 7.10 (4H, each d, each J=9 Hz, C$_6$H$_5$).

Isomer B2 crystallised from ethyl acetate as needles m.p. 190°-200° C. [α]$^{20}$=−27° (C=0.2MeOH); (Found: C, 62.0; H, 8.4; N, 7.6. C$_{19}$H$_{30}$N$_2$O$_3$S requires: C, 62.3; H, 8.3; N, 7.6%); δ(CDCl$_3$) 0.78 (6H, m, (CH$_3$)$_2$CH); 1.28 (3H, d, J=5 Hz, CH$_3$CHSH); 1.16 (3H, m, CH CH$_2$); 2.16 (1H, m, CHCO); 2.74 (3H, d, J=5 Hz, CH$_3$NH); 3.02 (3H, m, CHSH, CH$_2$C$_6$H$_4$) 3.76 (3H, s, CH$_3$O); 4.68 (1H, m, NHCHCO); 6.3 (1H, m, NH); 6.52 (1H, m, NH); 6.78 and 7.08 (3H, each d, each J=8 Hz, C$_6$H$_4$).

EXAMPLE 2

N-[2-(1-S-Mercaptobenzyl)-4-methylpentanoyl]-O-methyl-L-tyrosine-N-methylamide (a) E and Z Methyl 3-phenyl-2-(2-methylpropyl)-prop-2-enoate To a stirred solution of 4-Methyl-2-(diethylphosphono)pentanoic acid methyl ester (25.72 g, 96.3 mmole) in dry tetrahydrofuran (250 ml) under nitrogen was added sodium hydride (4.2 g, 60% dispersion in oil) portionwise. After stirring for 30 min. at room temperature benzaldehyde (11.22 g, 96.3 mmole) was slowly added and the reaction mixture was then stirred for a further hour at room temperature. Volatiles were then removed in vacuo and the residue was dissolved in ethyl acetate, washed with saturated aqueous ammonium chloride solution (250 ml×2), dried (sodium sulphate), filtered and evaporated in vacuo to an oil. Distillation under reduced pressure gave the title compound as an oil (16.6 g, 79%); (Found: C, 75.83; H, 8.38. $C_{14}H_{18}O_2+0.2 H_2O$ requires: C, 75.78; H, 8.36%); δ(CDCl$_3$) 0.87 and 0.95 (together 6H, each d, each J=7 Hz, (CH$_3$)$_2$CH); 1.90 (1H, m, (CH$_3$)$_2$CH); 2.34 and 2.52 (together 2H, each d, each J=8 Hz, CH$_2$CH(CH$_3$)$_2$); 3.82 (3H, s, OCH$_3$); 7.70 and 7.2–7.42 (together 6H, s, m, C$_6$H$_5$, vinyl CH).

(E and Z 3-Phenyl-2-(2-methylpropyl)-prop-2-enoic acid

The preceeding ester (15.66 g, 71 mmole) was dissolved in ethanol (300 ml) and to this was added a solution of sodium hydroxide (2.8 g) in water (70 ml). After stirring and heating under reflux overnight the reaction mixture was cooled and diluted with water. The reaction mixture was then concentrated in vacuo and washed with dichloromethane. The aqueous extract after acidification to pH 1 with concentrated hydrochoric acid was extracted with dichloromethane (250 ml×2) and this organic extract was dried (sodium sulphate), filtered and evaporated in vacuo to a solid (13.38 g, 91%); m.p. 66°–67.5°; (Found: C, 75.39; H, 7.92. $C_{13}H_{16}O_2+0.2H_2O$ requires C, 75.12; H, 7.95%); (CDCl$_3$) 0.90 and 0.98 (together 6H, each d, each J=7 Hz, (CH$_3$)$_2$CH); 1.95 (1H, m, (CH$_3$)$_2$CH); 2.34 and 2.52 (together 2H, each d, each J=8 Hz, (CH$_3$)$_2$CHCH$_2$); 7.84 and 7.26–7.42 (together 6H, s, m, C$_6$H$_5$, vinyl CH).

(c) 3-Phenyl-3-(S-acetyl)-2-(2-methylpropyl)-propanoic acid

A solution of the preceeding acid (12.58 g, 57.7 mmole) in thioacetic acid (65 ml) was heated under reflux for five days. The solution was then concentrated in vacuo and the residue was columned on silica eluting with dichloromethane in an increasing ethyl acetate gradient to give the title compound (7 g, 41%) as a mixture of isomers. Careful rechromatography of a portion of this material on silica eluting with the same solvent system gave the two separate enantiomeric pairs PAIR A m.p. 127°–129°; (Found: C, 62.38; H, 7.25. $C_{15}H_{20}O_3S+0.5H_2O$ requires C, 62.26; H, 7.31%); δ(CDCl$_3$) 0.9 (6H, dd, J=7 Hz, CH(CH$_3$)$_2$); 1.4–1.8 (3H, m, CH$_2$CH(CH$_3$)$_2$); 2.32 (3H, s, CH$_3$COS); 2.93 (1H, m, CHCO$_2$H); 4.77 (1H, d, J=10 Hz, C$_6$H$_5$CH) and 7.17–7.36 (5H, m, C$_6$H$_5$).

PAIR B m.p. 143°–144°; (Found: C, 63.73; H, 7.18. $C_{15}H_{20}O_3S+0.1H_2O$ requires C, 63.85; H, 7.22%); δ(CDCl$_3$) 0.83 (6H, d, J=7 Hz, (CH$_3$)$_2$CH); 1.08 (1H, m, CH$_2$CH); 1.5–1.75 (2H, m, CH$_2$CH); 2.28 (3H, s, CH$_3$COS); 3.04 (1H, dt, J=5 and 10 Hz, CHCO$_2$H); 4.79 (1H, d, J=10 Hz, C$_6$H$_5$CH) and 7.2–7.34 (5H, m, C$_6$H$_5$).

(d) N-[2-(1-S-Acetylmeercaptobenzyl)-4-methylpentanoyl]-O-methyl-L-tyrosine N-Methylamide
A ISOMERS The faster running pair of enantiomers from above (PAIR A) (700 mg, 2.5 mmole) was dissolved in dry DMF (10 ml) and to this cold (0°) stirred solution was added 1-hydroxybenzotriazole (400 mg, 2.5 mmole), N-ethyl-N'-(3-dimethylaminopropyl)carbodiimide hydrochloride (500 mg, 2.5 mmole) and N-methylmorpholine (275 mg, 2.75 mmole). O-Methyl -L-tyrosine N-methylamide hydrochloride (625 mg, 2.5 mmole) and N-methylmorpholine (275 mg, 2.75 mmole) were then added and the reaction mixture was allowed to stir and warm to room temperature over 64 h. Volatiles were then removed in vacuo and the residue was taken up in ethyl acetate, washed (saturated aqueous sodium bicarbonate solution, 3N citric acid and saturated aqueous sodium bicarbonate solution), dried, filtered and evaporated in vacuo to an oil. Chromatography of this material on silica eluting with dichloromethane in an increasing ethyl acetate gradient gave the two separate diastereoisomers.

ISOMER A1

(350 mg); m.p. 203°–206°; (Found: C, 66.54; H, 7.24; N, 5.80. $C_{26}H_{34}N_2O_4S$ requires C, 66.35; H, 7.28; N, 5.95%); δ(CDCl$_3$) 0.85 (6H, m, CH(CH$_3$)$_2$); 1.2–1.85 (3H, m, CH$_2$CH(CH$_3$)$_2$); 2.2–2.8 (3H, m, C$_6$H$_5$CHCHCO, CH$_2$C$_6$H$_4$); 2.32 (3H, s, COSCH$_3$); 2.58 (3H, d, J=5 Hz, CONHCH$_3$); 3.78 (3H, s, OCH$_3$); 4.25 (1H, q, J=6 and 14 HZ, α-CH); 4.74 (1H, d, J=10 Hz, C$_6$H$_5$CHS); 5.44 (1H, m, CONH); 6.48 (1H, d, J=8 Hz, CONH); 6.79 (2H, d, J=8 Hz, Tyr); 6.95 (2H, d, J=8 Hz, Tyr) and 7.16–7.44 (5H, m, C$_6$H$_5$).

ISOMER A2

(285 mg); m.p. 204°–207°; (Found: C, 65.71; H, 7.21; N, 5.87. $C_{26}H_{34}N_2O_4S+0.3H_2O$ requires C, 65.60; H, 7.33; N, 5.88%) δ(CDCl$_3$) 0.69 (3H, d, J=7 Hz, CH(CH$_3$)$_2$); ; 0.74 (3H, d, J=7 Hz, CH(CH$_3$)$_2$; 0.95 (1H, m, CH$_2$CH(CH$_3$)$_2$); 1.5 (2H, m, CH$_2$CH(CH$_3$)$_2$); 2.26 (3H, s, CH$_3$COS); 2.4 (3H, d, J=5 Hz, CONHCH$_3$); 2.50 (1H, m, C$_6$H$_5$CHCHCO); 2.82 (1H, dd, J=6 and 14 Hz, CHC$_6$H$_4$); 2.97 (1H, dd, J=6 and 17 Hz, CHC$_6$H$_4$; 3.75 (3H, s, OCH$_3$); 4.42 (1H, q, J=7 and 10 Hz, —CH); 4.70 (1H, d, J=11 Hz, C$_6$H$_5$CHS); 4.90 (1H, m, CONH); 5.45 (1H, d, J=8 Hz, CONH); 6.78 (2H, d, J=8 Hz, Tyr); 7.03 (2H, d, J=8 Hz, Tyr) and 7.18–7.4 (5H, m, C$_6$H$_5$).

B ISOMERS

The slower running pair of enantiomers from above (PAIR B) (650 mg, 2.32 mmole) was dissolved in dry DMF (8 ml) and to this cold (0°) stirred solution was added 1-hydroxybenzotriazole (355 mg, 2.32 mmole), N-ethyl-N'-(3-dimethylaminopropyl)carbodiimide hydrochloride (445 mg, 2.32 mmole) and N-methylmorpholine (235 mg, 2.32 mmole). O-methyl-L-tyrosine N-methylamide (483 mg, 2.32 mmole) and N-methylmorpholine (235 mg, 2.32 mmole) were then added and the reaction mixture was allowed to stir and warm to room temperature over 18 h. Volatiles were then removed in vacuo and the residue was taken up in ethyl acetate, washed (saturated aqueous sodium bicarbonate solution, 3N citric acid and saturated aqueous sodium bicarbonate solution), dried, filtered and evaporated in vacuo to an oil. Chromatography of this material on silica eluting with dichlormethane in an increasing ethyl acetate gradient gave the two separate disastereoisomers.

ISOMER B1

(300 mg); m.p. 219°–220° C.; (Found: C, 66.18; H, 7.33; N, 5.90. $C_{26}H_{34}N_2O_4S$ requires C, 66.35; H, 7.28; N, 5.95%); δ(CDCl$_3$) 0.75 (6H, d, J=7 Hz, CH(CH$_3$)$_2$);

1.05 (1H, m, CH$_2$CH(CH$_3$)$_2$); 1.2–1.68 (2H, m, CH$_2$CH(CH$_3$)$_2$); 2.24 (3H, s, COSCH$_3$); 2.72 (3H, d, J=5 Hz, CONHCH$_3$); 2.5–3.1 (3H, m, C$_6$H$_5$CH/CHCO, CH$_2$C$_6$H$_4$); 3.78 (3H, s, OCH$_3$); 4.63 (1H, q, J=5 and 14 Hz, α—CH); 4.75 (1H, d, J=10 Hz, C$_6$H$_5$CHS); 6.16 (1H, m, CONH); 6.55 (1H, d, J=7 Hz, CONH); 6.83 (2H, d, J=8 Hz, Tyr); 7.12 (2H, d, J=8 Hz, Tyr) and 7.15–7.44 (5H, m, C$_6$H$_5$).

ISOMER B2 m.p. 176°–177°; (Found: C, 65.01; H, 7.23; N, 5.77. C$_{26}$H$_{34}$N$_2$O$_4$S+0.5H$_2$O requires C, 65.11; H, 7.36; N, 5.84%); δ(CDCl$_3$) 0.65 (3H, d, J=7 Hz, CH(CH$_3$)); 0.70 (3H, d, J=7 Hz, CH(CH$_3$)); 0.76–1.15 and 1.44–1.62 (3H, m, CH$_2$CH(CH$_3$)$_2$); 2.24 (3H, s, COSCH$_3$); 2.65 (1H, m, C$_6$H$_5$CHCHCO); 2.75 (3H, d, J=5 Hz, CONHCH$_3$); 3.0 (2H, m, CH$_2$C$_6$H$_4$); 3.78 (3H, s, OCH$_3$); 4.68 (2H, m, C$_6$H$_5$CHS, α—CH); 6.05 (2H, m, CONH×2); 6.82 (2H, d, J=8 Hz, Tyr); 7.12 (2H, d, J=8 Hz, Tyr) and 7.2–7.35 (5H, m, C$_6$H$_5$).

(e) N-[2-(1-S-Mercaptobenzyl)-4-methylpentanoyl]-O-methyl-L-tyrosine N-Methylamide Each of the diastereoisomers A1, A2, B1, B2 were separately treated as follows:

To a solution of the isomer (120 mg, 0.25 mmole) in degassed methanol (6 ml) under argon was added dilute aqueous ammonium hydroxide solution (1 ml). After standing overnight at room temperature volatiles were removed in vacuo and the residue, after trituration with methanol/water and diethyl ether, was filtered and dried in vacuo. In this way was produced

ISOMER A m.p. 218°–220° C.; δ(CDCl$_3$) 0.90 (3H, d, J=7 Hz, CH(CH$_3$)); 0.91 (3H, d, J=7 Hz, CH(CH$_3$)); 1.44 (1H, m, CH(CH$_3$)$_2$); 1.68 (2H, m, CH$_2$CH(CH$_3$)$_2$); 1.98 (1H, d, J=5 Hz, SH); 2.17 (1H, dd, J=8 and 12 Hz, CHC$_6$H$_4$); 2.32 (1H, dd, J=5 and 12 Hz, CHC$_6$H$_4$); 2.57 (3H, d, J=5 Hz, CONHCH$_3$); 2.60 (1H, m, C$_6$H$_5$CHSCHCO); 3.77 (3H, s, OCH$_3$); 4.12 (2H, m, C$_6$H$_5$CHS, α—CH); 5.12 (1H, br, CONH); 5.94 (1H, d, J=7 Hz, CONH); 6.77 (2H, d, J=8 Hz, Tyr); 6.91 (2H, d, J=8 Hz, Tyr) and 7.2–7.42 (5H, m, C$_6$H$_5$).

ISOMER A2 m.p. 171°–174°; δ(CDCl$_3$) 0.75 (3H, d, J=7 Hz, CH(CH$_3$)); 0.80 (3H, d, J=7 Hz, CH(CH$_3$)); 0.95 (1H, m, CH(CH$_3$)$_2$); 1.56–1.70 (2H, m, CH$_2$CH(CH$_3$ $_2$); 1.91 (1H, d, J=5 Hz, SH); 2.41 (3H, d, J=5 Hz, CONHCH$_3$); 2.38–2.55 (1H, m, C$_6$H$_5$CHSCHCO); 2.75–2.92 (1H, dd, J=9 and 14 Hz, CHC$_6$H$_4$); 2.95–3.10 (1H, dd, J=9 and 14 Hz, CHC$_6$H$_4$); 3.79 (3H, s OCH$_3$); 4.04 (1H, dd, J=5 and 10 Hz, C$_6$H$_5$CHS); 4.24 (1H, q, J=7 and 14 Hz, α—CH); 4.80 (1H, br, CONH); 5.48 (1H, d, J=8 Hz, CONH); 6.80 (2H, d, J=8 Hz, Tyr); 7.02 (2H, d, J=8 Hz, Tyr) and 7.2–7.4 (5H, m, C$_6$H$_5$).

ISOMER B1 m.p. 222°–224°; δ(CDCl$_3$) 0.7 (3H, d, J=7 Hz, CH(CH$_3$)); 0.75 (3H, d, J=7 hz, CH(CH$_3$)); 1.27 (1H, m, CH(CH$_3$)$_2$); 1.50 (2H, dt, J=3 and 12 Hz, CH$_2$CH(CH$_3$)$_2$); 1.96 (1H, d, J=6 Hz, SH); 2.67 (1H, dt, J=3 and 10 Hz, C$_6$H$_5$CHSCHCO); 2.71 (3H, d, J=5 Hz, CONHCH$_3$); 2.99 (1H, dd, J=7 and 14 Hz, CHC$_6$H$_4$); 3.15 (1H, dd, J=7 and 14 Hz, CHC$_6$H$_4$); 3.78 (3H, s, OCH$_3$); 4.05 (1H, dd, J=6 and 10 Hz, C$_6$H$_5$CHS); 4.64 (1H, q, J=7 and 14 Hz, αCH); 5.70 (1H, br, CONH); 6.48 (1H, d, J=7 Hz, CONH); 6.83 (2H, d, J=8 Hz, Tyr); 7.19 (2H, d, J=8 Hz, Tyr) and 7.16–7.45 (5H, m, C$_6$H$_5$).

ISOMER B2 m.p. 88°–92°; δ(CDCl$_3$) 0.57 (3H, d, J=7 Hz, CH(CH$_3$)); 0.61 (3H, d, J=7 Hz, CH(CH$_3$); 0.92 (1H, m, CH(CH$_3$)$_2$); 1.45 (2H, dt, J=3 and 14 Hz, CH$_2$CH(CH$_3$)$_2$); 2.11 (2H, d, J=6 Hz, SH); 2.58 (1H, dt, J=3 and 12 Hz, C$_6$H$_5$CHSCHCO); 2.78 (3H, d, J=5 Hz, CONHCH$_3$); 3.06 (1H, dd, J=7 and 14 Hz, CHC$_6$H$_4$); 3.18 (1H, dd, J=7 and 14 Hz, CHC$_6$H$_4$); 3.79 (3H, s, OCH$_3$); d4.06 (1H, dd, J=6 and 12 Hz, C$_6$H$_5$CHSCHCO); 4.79 (1H, q, J=7 and 14 Hz, α—CH); 6.16 (1H, d, CONH); 6.48 (1H, br, CONH); 6.84 (2H, d, J=8 Hz, Tyr); 7.15 (2H, d, J=8 Hz, Tyr) and 7.08–7.43 (5H, m, C$_6$H$_5$).

EXAMPLE 3

N-(2-(1-Mercapto-2-methylpropyl)-4-methylpentanoyl)-O-methyl-L-tyrosine N-Methyl amide (a) E and Z 2-(2-methylpropyl)-4-methyl-pent-2-enoic acid Methyl ester 4-Methyl-2-(diethylphosphono)pentanoic acid methyl ester (28 g, 0.1M) prepared as in Example (1) in dry tetrahydrofuran (200 ml) was stirred under nitrogen whilst sodium hydride (2.2 g, 80% dispersion in oil; 0.11M) was added portion wise at 23° C. The reaction was stirred for 30 minutes and isobutyraldehyde (72 g, 1M) added with cooling to maintain the temperature below 30° C. The reaction was stirred for 16 h at 20° C. and water (20 ml) added. The organic phase was diluted with ether and then washed successively with aqueous sodium hydrogen carbonate, water and aqueous citric acid (1M), dried over sodium sulphate and concentrated in vacuo. Vacuum distillation of the resulting oil afforded E and Z 2-(2-methylpropyl)-4-methyl-pent-2-enoic acid methyl ester (12.5 g) b.p. 60°–70° C. at 0.5 mm Hg as a colourless oil δ(CDCl$_3$) 0.86 and 0.88 (6H, each d, each J=7 Hz CH$_2$CH(CH$_3$)$_2$); 1.0–1.02 (6H, each d, each J=7 Hz, CHCH(CH$_3$)$_2$); 1.6–1.85 (1H, m, CH$_2$CH) and 2.1 and 2.2 (2H, each d, each J=7 Hz, CH$_2$) 2.55 and 2.75 (1H, each m, C=CHCH); 3.74 (3H, s, OCH$_3$); 5.58 and 6.59 (1H, each d, each J=9 Hz, C=CH).

(b) E and Z 2-(2-methylpropyl)-4-methyl-pent-2-enoic acid

E and Z 2-(2-methylpropyl)4-methyl-pent-2-enoic acid (11.6 g, 65 mM) in methanol (200 ml) was treated with sodium hydroxide (12.6 g) in water (50 ml) under reflux for 17 h. The solution was concentrated in vacuo to a gum and redissolved in water (100 ml) washed with dichloromethane and then acidified to pH1 with concentrated hydrochloric acid. The aqueous solution was extracted with fresh dichloromethane and the organic phase separated dried over sodium sulphate and concentrated in vacuo to afford E and Z 2-(2-methylpropyl)-4-methyl-pent-2-enoic acid (8.77 g) as a pale yellow oil δ(CDCl$_3$) 0.88 and 0.91 (6H, each d, each J=7 Hz, CH$_2$CH(CH$_3$)$_2$); 1.02 and 1.04 (6H, each d, each J=7 Hz, CHCH(CH$_3$)$_2$); 1.78 (1H, m, CH); 2.1 and 2.21 (2H, each d, each J=7 Hz, CH$_2$); 2.6 and 3.3 (1H, each m, C=CH—CH); 5.74 and 6.75 (1H, each d, each J=9 Hz, CH=C) 10.3 (1H, m, OH).

(c) 2-(RS)-(1(RS)-S-Acetyl mercapto-2-methylpropyl)-4-methyl pentanoic acid

E and Z 2-(2-methylpropyl)-4-methyl-pent-2-enoic acid (7 g) in thioacetic acid (50 ml) was heated at 100° C. under reflux for 72 h. The excess thioacetic acid was removed in vacuo and the residue dissolved in dichloromethane which was extracted with aqueous saturated sodium hydrogen carbonate (3×200 ml). The aqueous phase was separated, acidified to pH1 with concentrated hydrochloric acid and extracted with fresh dichloromethane. The organic extract was dried over sodium sulphate and concentrated in vacuo to a gum which was chromatographed on silica in 15% ethyl acetate in dichloromethane to afford 2-(RS)-(1-(RS)-S-Acetyl mercapto-2-methylpropyl)-4-methyl pentanoic acid (2.0 g) as a colourless oil δ(CDCl$_3$) 0.86–1.08 (12H, m, 2×CH(CH$_3$)$_2$); 1.32–1.46 (1H, m, CH); 1.48–1.78 (2H, m, CH$_2$); 1.92–2.12 (1H, m, CH); 2.36 and 2.39 (3H, each s, CH$_3$COS); 2.65 and 2.9 (1H, each m, CH); 3.65 and 3.78 (1H, each m, CHS).

(d) N-[2-(1-S-Acetylmercapto-2-methylpropyl)-4-methyl pentanoyl]-O-methyl-L-tyrosine N-methyl amide 2-(RS)-(1-(RS)-S-Acetylmercapto-2-methylpropyl)-4-methyl pentanoic acid (1 g, 4.1 mM) in dichloromethane (10 ml) was treated with N-ethyl-N'-(3-dimethylaminopropyl)carbodiimide hydrochloride (0.86 g, 4.5 mM) 1-hydroxybenzotriazole (0.69 g 0.45 mM) and O-methyl-L-tyrosine N-methyl amide (0.94 g, 4.5 mM) at 0° C. with continuous stirring. The reaction was allowed to warm to 20° C. over 48 h, then diluted with dichloromethane and washed successively with aqueous saturated sodium hydrogen carbonate, water and aqueous citric acid (1M). The organic phase was dried over sodium sulphate and concentrated in vacuo to a gum (1.2 g). Column chromatography on silica in 25% ethyl acetate in dichloromethane afforded 2 main fractions. The first eluted pair of diastereomers was designated the A isomers.

A ISOMERS

Fraction 1 afforded N-[2-(1-S-Acetylmercapto-2-methylpropyl)-4-methyl pentanoyl]-O-methyl-L-tyrosine N-methyl amide (A isomers, 0.57 g) as a pair of diasterisomers which crystallised from ethyl acetate as needles m.p. 84°–89°; (Found: C, 63.8; H, 8.4; N, 6.4. C$_{23}$H$_{36}$N$_2$O$_4$S$_1$ requires: C, 63.3; H, 8.3; N, 6.42%). δ(CDCl$_3$) 0.74–1.0 (12H, m, 2×CH(CH$_3$)$_2$); 1.3 (2H, m, CH$_2$); 1.55 (1H, m, CH); 1.75 (1H, m, CH); 2.33 and 2.36 (3H, each s, CH$_3$COS); 2.55 (1H, m, CH); 2.74 (3H, m, NHCH$_3$); 3.0 (2H, m, CH$_2$C$_6$H$_4$); 3.54 and 3.65 (1H, each m, NHCHCO); 3.80 (3H, s, CH$_3$O); 4.56 and 4.7 (1H, one q, one m, CHS); 6.1 (1H, m, NH); 6.4 (1H, each d, each J=8 Hz, NH); 6.84, 7.12 and 7.13 (4H, each d, each J=9 Hz, C$_6$H$_4$).

B ISOMERS

Fraction 2 afforded N-(2-(1-S-Acetylmercapto-2-methylpropyl)-4-methylpentanoyl)-O-methyl-L-tyrosine N-methyl amide (B isomers, 0.14 g) which crystallised from ethyl acetate as needles m.p. 157.5°–158.5° (Found: C, 63.0, H, 8.4; N, 6.3. C$_{23}$H$_{36}$N$_2$O$_4$S$_1$ requires: C, 63.3; H, 8.3; N, 6.4%); δ(CDCl$_3$) 0.73–0.96 (12H, m, 2×CH(CH$_3$)$_2$); 1.1–1.32 (2H, m, CHCH$_2$CH); 1.54 (1H, t, J=10 Hz, CH); 1.98 (1H, q, J=7 Hz, CH); 2.33 (3H, s, CH$_3$CO); 2.5 (1H, m, CH); 2.72 (3H, d, J=5 Hz, NHCH$_3$); 2.99 (2H, d, J=8 Hz CH$_2$C$_6$H$_4$); 3.64 (1H, t, J=7 Hz, CHS); 3.78 (3H, s, OCH$_3$); 4.58 (1H, q, J-8 Hz NH—CH—CO); 5.98 (1H, d, J=5 Hz, NH); 6.11 (1H, d, J=7 Hz, NH); 6.83 and 7.13 (4H, each d, each J=9 Hz, C$_6$H$_4$).

(e) N-[2-(1-Mercapto-2-methylpropyl)-4-methylpentanoyl]-O-methyl-L-tyrosine N-methylamide Each of the two separated pairs of diastereoisomers of the foregoing S-acetyl compounds (110 mg) in methanol (10 ml) were treated with aqueous ammonia (30%, 1 ml) under an atmosphere of argon at 20° C. for 6 h. The solvent was then removed in vacuo and the residue triturated with ether to afford the required thiol (75 mg). Isomer A crystallised as needles m.p. 178°–185° C. (Found: C, 64.2; H, 8.67; N, 7.0. C$_{21}$H$_{34}$N$_2$O$_3$S requires: C, 63.9; H, 8.7; N, 7.1%) δ(CDCl$_3$) 0.76–1.06 (12H, m, 2×CH(CH$_3$)$_2$); 1.06–1.64 (4H, m, 2×CH, CH$_2$); 1.6 (1H, m, CH—CO) 2.74 (3H, m, NHCH$_3$), 3.02 (2H, m, CH$_2$C$_6$H$_4$O; 3.78 (3H, s QCH$_3$); 4.66 (1H, m, NHCHCO); 6.02 (1H, m, NH); 6.34 and 6.4 (1H, each m, NH); 6.8 and 7.12 (4H, each d, each J=8 Hz, C$_6$H$_4$).

"Isomer B" crystallised as needles m.p. 150°–155° C. (Found: C, 64.0; H, 8.8; N, 6.9; C$_{21}$H$_{34}$N$_2$O$_3$S$_1$ requires: C, 63.9; H, 8.7; N, 7.1%); δ(CDCl$_3$) 0.68 and 1.0 (6H, each d, each J=6 Hz, CH(CH$_3$)$_2$); 0.76 (6H, d, J=6 Hz, CH(CH$_3$)$_2$) 0.75–1.75 (4H, m, 2×CH, CH$_2$); 2.08 (1H, m, CHCO); 2.76 (3H, d, J=4 Hz, NHCH$_3$); 3.78 (3H, s, CH$_3$O); 4.8 (1H, m, NHCHCO); 5.8 (1H, m, NH); 6.72 (1H, m, NH); 6.8 and 7.12 (4H, each d, each J=7 Hz, C$_6$H$_4$).

EXAMPLE 4

N-[2[1-Mercaptoethyl]-octanoyl]-O-methyl-L-tyrosine]N-Methylamide (a) 2-(Diethylphosphono)octanoic acid Ethyl ester 2-Bromo octanoic acid ethyl ester (50 g, 0.2M) was heated at 150° with triethyl phosphite (75 g, 0.44M) and the distillate, Bpt 37°–60° condensed as the temperature was raised to 200° over 6 h. The reaction mixture was cooled and distilled under high vacuum (1.00 mm Hg) to afford 2 main fractions (a) Triethyl phosphite b.p. 40°–70° and (b) 2-(diethylphosphono)octanoic acid ethyl ester (49.5 g, 0.16M); b.p. 120°–130° at 0.5 mm Hg. (Found: C, 52.9; H, 9.4. C$_{14}$H$_{29}$O$_5$P+0.5H$_2$O requires: C, 53.0; H, 9.5%; δ(CDCl$_3$) 0.88 (3H, m, CH$_3$); 1.32 (17H, m, (CH$_2$)$_4$, 3×CH$_3$); 1.9 (2H, m, CH$_2$); 2.92 (1H, d, d, d, J=22 Hz, J=10 Hz, J=4 Hz, CH—P); 4.18 (6H, m, 3×CH$_2$O).

(b) E and Z ethyl(2-hexyl)but-2-enoate 2-(Diethylphosphono)octanoic acid ethyl ester (28 g, 0.09M) in dry THF (150 ml) was treated with sodium hydride (3.3 g, 80%) 0.11M) under at atmosphere of argon at 0° with continuous stirring. The reaction was allowed to warm to 20° over 1 h. The reaction was then cooled to −30° and acetaldehyde (13 g, 0.29M) in dry tetrahydrofuran (100 ml) added dropwise. The reaction was warmed to 20° C. and 3 h and concentrated in vacuo to a gum. The residue was taken up in dichloromethane and washed with aqueous saturated sodium hydroxide carbonate. The organic layer was separated, dried over sodium sulphate and concentrated in vacuo to a gum which was distilled in vacuo. E and Z ethyl(2-hexyl)but-2-enoate distilled as the main fraction (14 g, 0.07M), b.p. 60°–70° C. at 0.5 mm Hg. (Found: C, 67.6; H, 10.4 C$_{12}$H$_{22}$O$_2$+0.9H$_2$O requires: C, 67.2; H, 11.2%); δ(CDCl$_3$) 0.88 (3H, m, CH$_3$); 1.3 (11H, m, (CH$_2$)$_4$, CH$_3$) 1.8 and 1.96 (3H, each d, each J=8 Hz, CH$_3$CH); 2.3 (2H, m, CH$_2$C) 4.2 (2H, q, J=8 Hz, CH$_2$O); 5.94 and 6.8 (1H, each q, each J=8 Hz, CH).

(c) E and Z (2-Hexyl)but-2-enoic acid

Ethyl (2-hexyl)but-2-enoate (12 g, 0.06M) in methanol (150 ml) was treated with sodium hydroxide (15 g, 0.375M) in water (100 ml) under reflux for 6 hours. The solvents were then removed in vacuo and the residue taken up in water and extracted with dichloromethane. The aqueous phase was separted, acidified in pH1 with concentrated hydrochloric acid and extracted with dichloromethane. The extract was dried over sodium sulphate and concentrated in vacuo to an oil which was distilled in vacuo to afford E and Z (2-hexyl)but-2-enoic acid (10.1 g, 0.06M) as the main fraction (b.p. 100°–110° C. at 0.5 mm Hg) (Found: C, 68.2; H, 10.4. $C_{10}H_{18}O_2 + 0.5H_2O$ requires: C, 68.5; H, 9.7%); $\delta(CDCl_3)$ 0.88 (3H, m, $CH_3$); 1.3 (8H, m, $(CH_2)_4$); 1.84 and 2.04 (3H, each m, each $CH_3CH$); 2.32 (2H, t, J=8 Hz, $CH_2$) 6.14 and 6.94 (1H, each q, each J=8 Hz, CH).

(d) 2(1-S-Acetyl mercaptoethyl)octanoic Acid (2-Hexyl)but-2-enoate (9 g, 45 mM) was heated at 110° C. with redistilled thioacetic acid (20 g) under reflux for 24 h. The excess thioacetic acid was removed in vacuo and the residue dissolved in dichloromethane. The orgaic layer was extracted five times with aqueous saturated sodium hydrogen carbonate solution (250 ml) and the combined aqueous extracts acidified to pH1 with dil. hydrochloric acid and extracted with dichloromethane. The organic extract was dried over sodium sulphate and concentrated in vaccuo to afford 2(1-S-Acetylmercaptoethyl)octanoic acid (8.9 g, 36 mM) as a gum. (Found: C, 58.25; H, 9.12. $C_{12}H_{22}O_3S$ requires: C, 58.5; H, 9.0%); $\delta(CDCl_3)$ 0.88 (3H, t, J=9 Hz, $CH_3CH_2$); 1.14–1.8 (10H, m, $(CH_2)_5$); 2.34 (3H, s, $C\overline{H}_3COS$); 2.58 (1H, m, CHCO); 3.82 (1H, m, CHS).

(e) N-[2-(1-S-Acetylmercaptoethyl)octanoyl]-O-methyl-L-tyrosine t-Butyl ester 2-(1-S-Acetyl mercaptoethyl)octanoic acid (4 g, 16 mM) in dichloromethane (25 ml) was treated with 1-hydroxybenzotriazole (2.8 g, 0.018M), O-methyl tyrosine t-butyl ester (4.6 g, 18 mM) and N-ethyl-N'-(3-dimethylaminopropyl)carbodiimide hydrochloride (3.6 g 18 mM) at 0° C. with continuous stirring. The reaction was allowed to warm to room temperature overnight and then diluted with dichloromethane washed with aqueous saturated sodium bicarbonate and 3N citric acid and dried over sodium sulphate. The solution was concentrated in vacuo to a gum which was chromatographed on silica in a gradient of 20% ether in hexane to 50% ether in hexane. The main fraction eluting in 40% ether afforded N-[2-(1-S-Acetylmercaptoethyl)-1-oxooctyl]-O-methyl-L-tyrosine t-Butyl ester, (6.5 g 14 mM, as a gum containing all 4 isomers.

(f) N-[2-(1-S-Acetylmercaptoethyl)octanoyl]-O-methyl-L-tyrosine N-methylamide

N-[2-(1-S-Acetyl mercaptoethyl)]octanoyl-O-methyl-L-tyrosine t-Butyl ester (5 g, 0.01M) in dichloromethane (20 ml) was treated with trifluroacetic acid (20 ml) at 20° C. for 2 h. The solvents were removed in vacuo with the residue dissolved in dichloromethane (100 ml) and adjusted to neutrality with N-methylmorpholine. The solution was cooled to 0° C. and treated with 1-hydroxy benzotriazole (1.66 g, 11 mM), methylamine hydrochloride (0.9 g, 13 mM) and n-ethyl-N'-(3-dimethylaminopropyl)carbodiimide hydrochloride (2.1 g 11 mM) with continuous stirring. The reaction was adjusted to pH7 with N-methylmorpholine and allowed to warm to 20° C. over 16 h. The solution was then diluted with dichloromethane and washed successively with aqueous saturated sodium hydrogen carbonate, water, and aqueous citric acid (1M), dried over sodium sulphate and concentrated in vacuo to a gum. Column chromatography on silica in a gradient of 30% to 70% ethyl acetate in dichloromethane afforded two main fractions. Elution in 50% ethyl acetate in dichloromethane afforded N-[2-(1-S-Acetylmercaptoethyl)octanoyl]-O-methyl-L-tyrosine N-methylamide as a "PAIR A" of diastereoisomers (1.6 g) which crystallised from ether as needles m.p. 138°–142° C. (Found: C, 63.3; H, 8.3; N, 6.4; $C_{23}H_{36}N_2O_4S$ requires: C, 63.3; H, 8.3; N, 6.4%); $\delta(CDCl_3)$ 0.86 (3H, t, J=7 Hz $CH_3CH_2$); 1.12 and 1.2 (3H, each d, each J=6 Hz, $CH_3C\overline{H}S$), 1.04–1.74 (10H, m, $(CH_2)_5$); 2.24 (1H, m, $CHC\overline{O}$); 2.3 (3H, s, $CH_3COS$); 2.7 and 2.72 (3H, each d, each J=4 Hz, $NHCH_3$); 3.0 (2H, m, $CH_2C_6H_4$); 3.66 (1H, m, CHS), 3.76 and 3.78 (3H, each s, $CH_3O$); 4.64 (1H, q, J=8 Hz, $NHC\overline{H}CO$); 6.04 and 6.16 (1H, each m, NH) 6.4 and 6.76 ($1\overline{H}$, each d, each J-8 Hz, NH); 6.76 and 7.1 (2H, each d, each J=8 Hz, $C_6H_4$). Elution with 60% ethyl acetate in dichloromethane afforded N-[2-(1-S-Acetylmercaptoethyl)octanoyl]-O-methyl-L-tyrosine N-methylamide "PAIR B" of diastereoisomers, (1.1 g) which crystallized from ether as needles m.p. 160°–170° C. (Found: C, 63.4; H, 8.4; N, 6.5. $C_{23}H_{36}N_2O_4S$ requires C, 63.3; H, 8.3; N, 6.4%); $\delta(CDCl_3)$ 0.88 (3H, t, J=7 Hz, $CH_3CH_2$); 0.94–1.74 (10H, m, $(CH_2)_5$); 1.2 and 1.26 (3H, each d, each J=7 Hz, $CH_{3C}S$); 2.22 (1H, m, CHCO); 2.3 (3H, s, $CH_3COS$); 2.74 (3H, d, J=4 Hz, $CH_3NH$); 3.0 (2H, d, J=8 Hz, $CH_2C_6H_4$); 3.66 (1H, t, $J\overline{=}7$ Hz, CHS) 3.76 (3H, s, $CH_3\overline{O}$); 4.64 (1H, q, J=7 Hz $NHC\overline{H}CO$); 6.1 and 6.18 (1H, each m, NH); 6.32 and 6.44 ($1\overline{H}$, each d, J=9 Hz, NH); 6.76 and 7.08 (2H, each d, each J=8 Hz, $C_6H_4$).

(g) N-[2-(1-Mercaptoethyl)-1-octanoyl]-O-methyl-L-tyrosine N-methylamide

The A pair of isomers and the B pair of isomers were separately deprotected to afford the title compound as 'A isomers' and 'B isomers' by identical procedures as described below.

N-[-2-(1-S-Acetylmercaptoethyl)octanoyl]-O-methyl-L-tyrosine N-methylamide (500 mg, 1.15 mM) in methanol (10 ml) was treated with 40% aqueous ammonia solution (5 ml) under an atmosphere of argon at 20° C. for 16 h. The solvent was then removed in vacuo and the residue triturated with ether to afford N-[2-(1-mercaptoethyl)octanoyl]-O-methyl-L-tyrosine N-methylamide as ("PAIR A" of isomers) (320 mg) m.p. 190°–195° C. (Found: C, 63.0; H, 8.7; N, 7.1. $C_{21}H_{34}N_2O_3S + 0.25H_2O$ requires: C, 63.2; H, 8.7; N, 7.0%); $\delta(CDCl_3)$ 0.86 (3H, t, J=7 Hz, $CH_2CH_3$); 1.16 and 1.32 (3H, each d, each J=5 Hz, $CH_3CHS\overline{H}$); 1.22 and 1.38–1.72 (10H, m, $(CH_2)_5$); 2.08 ($1\overline{H}$, m, —CHCO); 2.74 (3H, d, $CH_3NH$); 3.02 (3H, m, CHSH, $CH_2C_6H_5$); 3.76 (3H, s, $\overline{C}H_3O$); 4.62 (1H, d, d, $J\overline{=}6$ Hz, $\overline{NH}CHCO$); 6.06 (1H, m, NH); 6.42 (1H, t, J=7 Hz, NH); 6.76 and 7.1 (2H, each d, each J=8 Hz, $C_6H_4$). The "PAIR B" of isomers afforded N-[2-(1-mercaptoethyl)octanoyl]-O-methyl-L-tyrosine N-methylamide as "PAIR B" of isomers (320 mg) m.p. 198°–200° C. (Found: C, 63.4; H, 8.7; N, 7.1. $C_{21}H_{34}O_3N_2S + 0.25H_2O$ requires: C, 63.2; H, 8.7; N, 7.0%); $\delta(CDCl_3)$ 0.88 (3H, t, J=7 Hz, $CH_2CH_3$); 1.3 and 1.36 (3H, each d, each J=6 Hz, $CH_3C\overline{H}SH$); 0.94–1.76 (10H, m, $(CH_2)_5$); 2.04 (1H, m, $C\overline{H}CO$); 2.74 and 2.75 (3H, each d, each J=5 Hz, $CH_3HN\overline{)}$; 3.12 (3H, m, CHSH, $CH_2C_6H_4$) 3.78 (3H, s, $OCH_3$); 4.6 (1H, m, $NHC\overline{H}CO$) 6.04 and 6.26 (1H, each m, NH) 6.78 and 7.1 (2H, each d, each J=8 Hz, $C_6H_4$).

EXAMPLE 5

N-[2-(1-Mercaptoethyl)hexanoyl]-O-methyl-L-tyrosine N-methyl amide (a) 2-diethylphosphono)hexanoic acid methyl ester 2-Bromohexanoic acid methyl ester (90 g, 0.43M) and triethyl phoshite (150 g, 0.9M) were heated at 105° C. and the distillate, B.p. 37°–60° C. was collected as the temperature was raised to 200° C. over 6 h. The reaction was cooled to 20° C. and distilled under high vacuum (0.5 mm Hg) to afford 2 main fractions (a) triethyl phoshite b.p. 50°–100° C. and (b) 2-(diethylphosphono)-hexanoic acid methyl ester (67.5 g, 0.25M) b.p. 100°–115° C. at 0.5 mm Hg. (Found: C, 48.0; H, 9.1. $C_{11}H_{23}O_5P_1 + 0.5H_2O$ requires: C, 48.0; H, 8.8%); $\delta(CDCl_3)$ 0.9 (3H, t, J-7 Hz, $CH_3$); 1.34 (10H, m, $2 \times CH_3$, $2 \times CH_2$); 1.9 (2H, m, $CH_2$); 2.98 (1H, d, d, d, J=23 Hz, J-12 Hz, J=4 Hz, CHP); 3.76 (3H, s, $CH_3$); 4.16 (4H, m, $2 \times CH_2O$).

(b) E and Z 2(butyl)but-2-enoic acid methyl ester

To 2-(diethylphosphono)hexanoic acid methyl ester (53.2 g, 0.2M) in dry tetrahydrofuran (300 ml) was added sodium hydride (5.3 g, 0.22M) under an atmosphere of argon at 0° C. with continuous stirring. The reaction was allowed to warm to room temperature over 1 hour when the evolution of hydrogen had ceased. The reaction was then cooled to −30° C. and acetaldehyde (30 g, 0.66M) added dropwise to the continuously stirred solution over 10 minutes. The reaction was allowed to warm to 20° C. over 16 h and then concentrated in vacuo to a gum which was dissolved in ether. The etherial solution was washed with aqueous saturated sodium hydrogen carbonate, dried over sodium sulphate and concentrated in vacuo. Vacuum distillation of the resulting gum afforded E and Z 2-(butyl)-but-2-enoic acid methyl ester (7.8 g) B.p. 50°–60° C. at 0.8 mm Hg (Found: C, 65.0; H, 10.1 $C_9H_{16}O_2 + 0.5H_2O$ requires: C, 65.4; H, 10.4%); $\delta(CDCl_3)$ 0.84 (3H, t, J=8 Hz, $CH_3CH_2$); 1.34 (4H, m, $2 \times CH_2$); 1.8 and 1.96 (3H each d, each J=7 Hz, $CH_3CH$); 2.32 (2H, m, $CH_2$—C); 3.72 and 3.74 (3H, each s, $CH_3O$); 5.96 and 6.84 (1H, each q, each J=7 Hz, CH).

(c) E and Z 2-(butyl)but-2-enoic acid

E and Z 2-Butyl)but-2-enoic acid methyl ester (7.5 g) in methanol (50 ml) was treated with aqueous sodium hydroxide (10 g in 20 ml) under reflux for 16 h. The solution was concentrated in vacuo to a gum, diluted with water and extracted with dichloromethane. The aqueous solution was separated acidified to pH 1 with concentrated hydrochloric acid and extracted with dichloromethane which was dried over sodium sulphate and concentrated in vacuo. Vacuum distillation of the resulting oil afforded E and Z 2-(butyl)but-2-enoic acid (5.1 g), b.p. 100°–105° C. at 0.6 mm Hg (Found: C, 65.61; H, 10.0. $C_8H_{14}O_2 + 0.25 H_2O$ requires: C, 65.5; H, 10.0%); $\delta(CDCl_3)$ 0.92 (3H, t, J=7 Hz, $CH_3CH_2$); 1.38 (4H, m, $2 \times CH_2$); 1.84 and 2.04, (3H, each d, each J=7 Hz, $CH_3CH$); 2.32 (2H, m, $CH_2$); 6.14 and 6.98 (1H, each q, each J=7 Hz, CH).

(d) 2-(RS)-1(RS)-S-Acetylmercaptoethyl-hexanoic Acid

E and Z-2-(butyl)-but-2-enoic acid (5 g) in thioacetic acid (20 ml) was heated under reflux for 26 h. The excess thiol acetic acid was removed in vacuo and the residue dissolved in dichloromethane. The organic solution was extracted with aqueous saturated sodium hydrogen carbonate (3×200 ml) and the combined aqueous extracts acidified to pH 1 with concentrated hydrochloric acid. The aqueous extracts were themselves extracted with dichloromethane and the organic solution dried over sodium sulphate and concentrated in vacuo to afford 2-(RS)-(1-(RS)-1-S-Acetylmercaptoethyl)-hexanoic acid (4.5 g) as a pale yellow gum. $\delta(CDCl_3)$ 0.9 (3H, m, $CH_3$); 1.36 (7H, m, $2 \times CH_2$, $CH_3$); 1.68 (2H, m, $CH_2$); 2.32 (3H, S, $CH_3COS$); 2.56 (1H, m, CHCO); 3.82 (1H, m, CHS).

(e) N[2-(1-S-Acetylmercaptoethyl)-hexanoyl]-O-methyl-L-tyrosine N-methylamide 2-(RS)-(1-(RS)-S-Acetylmercaptoethyl)hexanoic acid (4 g, 18.3 mM) in dichloromethane (50 ml) was treated with N-ethyl-N'-(3-dimethylaminopropylcarbodiimide hydrochloride (3.5 g, 18.3 mM), 1-hydroxybenzotriazole (2.8 g, 18.6 mM) and O-methyl L-tyrosine N-methylamide (4 g, 19.2 mM) at 0° C. with continuous stirring. The reaction was allowed to warm to 20° C. over 48 h. The reaction was diluted with dichloromethane and washed with aqueous saturated sodium hydrogen carbonate, water and aqueous citric acid (1 M). The organic phase was dried over sodium sulphate and concentrated in vacuo to a gum which was chromatographed on a silica column in a gradient of 30% ethyl acetate in dichloromethane to 60% ethyl acetate in dichloromethane to afford two pairs of diastereoisomers. The faster running pair N[2-(1-S-Acetylmercaptoethyl)-hexanoyl]-O-methyl-L-tyrosine N-methyl amide (Pair A 1.35 g) crystallised from ethyl acetate/ether as needles m.p. 135°–140° C. (Found: C, 61.9; H, 8.0; N, 6.8. $C_{21}H_{32}N_2O_4S_1$ requires: C, 61.7; H, 7.9; N, 6.9%); $\delta(CDCl_3)$ 0.84 (3H, s, $CH_3$); 1.12 and 1.18 (3H, each d, each J=8 Hz, $CH_3CH$); 1.26 (4H, m, $2 \times CH_2$); 1.62 (2H, m, $CH_2$); 2.26 (1H, m, CH); 2.3 (3H, s, $CH_3$); 2.73 and 2.75 (3H, each d, each J-4 Hz, $CH_3NH$); 3.02 (2H, m, $CH_2C_6H_4$); 3.6 (1H, m, CHS); 3.78 (3H, s, $OCH_3$); 4.64 (1H, 1, J=8 Hz, NHCHCO); 6.12 and 6.24 (1H, each m, NH); 6.4 and 6.58 (1H, each d, each J=9 Hz, NH); 6.8 and 7.14 (4H, each d, each J-8 Hz, $C_6H_4$).

The slower running pair N[2-(1-S-Acetylmercaptoethyl)-hexanoyl]-O-methyl-L-tyrosine N-methyl amide (Pair B 1.2 g) which crystallised from ethyl acetate/ether as needles m.p. 150°–155° C. (Found: C, 61.8; H, 8.0; N, 6.8. $C_{21}H_{32}N_2O_4S_1$ requires: C, 61.7; H, 7.9; N, 6.9%); $\delta(CDCl_3$ 0.82 (3H, s, $CH_3$); 1.26 and 1.3 (3H, d, J=7 Hz, $CH_3CH$); 1.02–1.6 (6H, m, $3 \times CH_2$); 2.24 (1H, m, CHCO); 2.32 (3H, s, $CH_3COS$); 2.76 (3H, m, $CH_3NH$); 3.02 (2H, d, J=7 Hz, $CH_2C_6H_4$); 3.8 (1H, m, CHS); 3.78 (3H, s, $OCH_3$); 4.68 (1H, quintet, J=6 Hz NHCH CO); 6.32 and 6.78 (1H, each m, NH); 6.42 and 6.54 (1H, each d, each J=7 Hz, NH); 6.78 and 7.12 (4H, each d, each J=8 Hz, $C_6H_4$).

(f) N[2-(1-S-Mercaptoethyl)hexanoyl]-O-methyl-L-tyrosine N-methylamide

The two pairs or separated diastereoisomers of the foregoing S-acetyl compounds (200 mg each) were individually dissolved in methanol (20 ml) and treated with 30% aqueous ammonia (5 ml) under an atmosphere of argon at 20° C. for 1 h. The solvents were evaporated in vacuo and the residue triturated with ether to afford the required thiol (150 mg). N-[2-(1-S-Mercaptoethyl)-hexanoyl]-O-methyl-L-tyrosine N-methyl amide (Pair A) which crystallised from ethyl acetate/ether as needles m.p. 193°–196° C. (Found: C, 59.6; H, 8.2; N, 8.7. $C_{19}H_{30}N_2O_3S_1 + 0.7 H_2O$ requires: C, 60.1; H, 8.3; N 7.4%); δ(CDCl$_3$) 0.86 (3H, t, J=8 Hz, CH$_3$; 1.14–1.78 (6H, m, 3×CH$_2$); 1.2 and 1.34 (3H, each d, each J=8 Hz, CH$_3$NH); 2.10 (1H, m, CHCO); 2.74 (3H, d, J=4 Hz, CH$_3$NH); 3.06 (3H, m, CH$_2$C$_6$H$_4$CHS); 3.78 (3H, s, CH$_3$O); 4.62 (1H, q, J=8 Hz, NHCHCO); 5.94 (1H, m, NH); 6.38 (1H, m, NH); 6.8 (2H, d, J=8 Hz, C$_6$H$_4$); 7.14 and 7.1 (2H, each d, each J-8 Hz C$_6$H$_4$).

N-[2-(1-S-Mercaptoethyl)hexanoyl]-O-methyl-L-tyrosine N-methylamide (Pair B) which crystallised from ethyl acetate/ether as needles m.p. 198°–202° C. (Found: C, 62.2; H, 8.2; N, 7.8. C$_{19}$H$_{30}$N$_2$O$_3$S$_1$ requires: C, 62.3; H, 8.3; N, 7.6%); δ(CDCl$_3$) 0.82 (3H, m, CH$_3$); 0.88–1.72 (6H, m, 3×CH$_2$); 1.3 and 1.36 (3H, each d, each 7 Hz, CH$_3$CH) 2.04 (1H, m, CH); 2.76 (3H, d, J=4 Hz, CH$_3$NH); 3.04 (3H, m, CH$_2$C$_6$H$_4$, CHS); 3.78 (3H, s, OCH$_3$); 4.7 (1H, m, NHCHCO); 6.28 and 6.36 (1H, each m, NH); 6.58 (1H, m, NH); 6.78 and 7.1 (4H, each d, each J=8 Hz, C$_6$H$_4$).

EXAMPLE 6

N-[2-(1-Mercaptoethyl)-4-methylpentanoyl]-O-benzyl-L-threonine N-Methylamide (a) N-[2-(1-S-Acetylmercaptoethyl)-4-methylpentanoyl]-O-benzyl-L-threonine To a solution of 2-(RS)-(1-S-acetylmercaptoethyl)-4-methylpentanoic acid prepared as described in Example 1 (500 mg, 2.4 mM) in dichloromethane (10 ml) stirred at 0° was added 1-hydroxybenzotriazole (398 mg, 2.6 mM), O-benzyl-L-threonine N-methylamide (577 mg, 2.6 mM), N-ethyl-N'-(3-dimethylaminopropyl)carbodiimide hydrochloride (499 mg, 2.6 mM) and finally N-methylmorpholine (262 mg, 2.6 mM). After 16 h at 20° the mixture was diluted with dichloromethane (10 ml) and washed in turn with saturated sodium hydrogen carbonate solution, water, citric acid (1M) and finally aqueous saturated sodium chloride. The material isolated from the organic layer was purified by chromatography on silica in 4:1 dichloromethane-ethyl acetate to give the desired peptide as two separated pairs of diastereoisomers. The faster running pair ("PAIR A") of diastereoisomers (0.20 g) had an Rf=0.52 in 1:1 dichloromethane ethyl acetate, m.p. 106°–131° C.; (Found: C, 62.4; H, 8.2; N, 6.7 C$_{22}$H$_{34}$N$_2$O$_4$S requires C, 62.5; H, 8.1; N, 6.6%); δ(CDCl$_3$) 0.88 and 0.9 (6H, each d, each J=8 Hz, (CH$_3$)$_2$C); 1.14, (3H, d, J=8 Hz, CH$_3$CHO); 1.3 and 1.32 (3H, each d, each J=7 Hz, CH$_3$CHS); 1.2 to 1.84 (3H, m, CH$_2$CH); 2.3 and 2.32 (3H, each s, CH$_3$COS); 2.48 (1H, m, CHCO); 2.82 (3H, d, J=5 Hz, CH$_3$NH); 3.72 (1H, t, J=7 Hz, CHS); 4.12 (1H, m, CHO); 4.56 (1H, m, NHCHCO); 4.66 (2H, s, CH$_2$C$_6$H$_5$); 6.44 (1H, m, NH); 6.66 and 6.72 (1H, each m, NH); 7.3 (5H, m, C$_6$H$_5$).

The slower running pair ("PAIR B") of diastereoisomers (0.24 g) had Rf=0.44 in 1:1 dichloromethane-ethyl acetate, m.p. 128°–143° C. (Found: C, 61.6; H, 8.1; N, 6.5. C$_{22}$H$_{34}$N$_2$O$_4$S+0.5 H$_2$O requires: C, 61.2; H, 8.2 N, 6.5%); δ(CDCl$_3$) 0.9 (6H, m, (CH$_3$)$_2$C); 1.1 (3H, d, J=7 Hz, CH$_3$CHO); 1.34 and 1.36 (3H, each d, each J=8 Hz, CH$_3$CHS); 1.18 to 1.86 (3H, m, CH$_2$CH); 2.32 (3H, s, CH$_3$COS); 2.5 (1H, m, CHCO); 2.84 (3H, d, J=5 Hz, CH$_3$NH); 3.74 (1H, m, CHS); 4.2 (1H, m, CHO); 4.52 (1H, m, NHCHCO); 4.62 and 4.3 (2H, each s, CH$_2$C$_6$H$_5$), 6.52 and 6.7 each (1H, m, NH); 7.3 (5H, m, C$_6$H$_5$).

(b) N-[2-(1-Mercaptoethyl)-4-methylpentanoyl]-O-benzyl-L-threonine N-Methylamide The first pair of diastereoisomers ("PAIR A") of the foregoing S-acetyl compound (0.15 g) in degassed methanol (10 ml) was treated under an atmosphere of nitorgen with 30% aqueous ammonia solution (2 ml) for 24 h. The reaction mixture was lyophilised over 24 h to give the required thiol (0.1 g) as a white powder containing a pair of diastereoisomers ("PAIR A"), m.p. 156°–159°; (Found: C, 62.65; H, 8.5; N, 7.3 C$_{20}$H$_{32}$N$_2$O$_3$S requires: C, 63.1; H, 8.5; N, 7.4%); δ(CDCl$_3$) 0.92 (6H, m, (CH$_3$)$_2$CH); 1.14 and 1.15 (3H, each d, each J=6 Hz, CH$_3$CHSH); 1.36 (3H, d, J=6 Hz, CH$_3$); 1.58 (3H, m, CH$_2$CH); 2.3 (1H, m, CHCO); 2.82 (3H, d, J=5 Hz, NHCH$_3$); 3.12 (1H, m, CHO); 4.14 (1H, m, CHS), 4.86 (1H, m, NHCHCO) 4.66 (2H, s, CH$_2$C$_6$H$_5$); 6.48 (1H, m, NH); 6.7 (1H, m, NH) and 7.32 (5H, m, C$_6$H$_5$). The ratio of the peaks at 1.14 and 1.15 was such as to indicate an isomer ratio of 2:1.

The second pair of diastereoisomers ("PAIR B") of the S-acetyl compound prepared in part (a) was treated in an identical way to give the desired thiol again as a mixture of two diastereoisomers ("PAIR B"), (0.1 g) m.p. 166°–169°; (Found: C, 62.6; H, 8.5; N, 7.2. C$_{20}$H$_{32}$N$_2$O$_3$S requires C, 63.1; H, 8.5; N, 7.4%); δ(CDCl$_3$) 0.94 (6H, m, (CH$_3$)$_2$CH); 1.12 and 1.18. (3H, each d, each J=6 Hz CH$_3$CHSH); 1.38 and 1.42 (3H, each d, each J=6 Hz, CHCHO); 1.72 (3H, m, CH$_2$CH); 2.32 (1H, m, CHCO); 2.78 (3H, d, J=5 Hz NHCH$_3$); 3.12 (1H, m, CHO); 4.2 (1H, m, CHS); 4.56 (1H, m, NHCHCO); 4.62 (2H, s, CH$_2$C$_6$H$_5$); 6.6 (1H, m, NH); 6.7 (1H, m, NH) and 7.32 (5H, m, C$_6$H$_5$). Again the ratio of the peaks at 1.12 and 1.18 (and repeated at 1.38 and 1.42) indicated a 2:1 ratio of two diastereoisomers.

EXAMPLE 7

N-[2-(1-S-Mercaptoethyl)-4-methyl-pentanoyl]-L-alanine N-butylamide (a) N-[2-(1-S-Acetylmercaptoethyl)-4-methyl-pentanoyl]-L-alanine O t-Butyl ester To a cold, (0°), stirred solution of 2-(RS)-(1-(RS)-S-Acetylmercaptoethyl)-4-methyl-pentanoic acid (2.63 g, 12.5 mmole) in dichloromethane (30 ml) was added 1-hydroxybenzotriazole (2.14 g, 14 mmole), N-ethyl-N'-(3-dimethylaminopropyl) carbodiimide hydrochloride (2.69 g, 14 mmole) and N-methylmorpholine (1.41 g, 14 mmole). After 15 min. at 0° a solution of L-alanine O t-butyl ester (1.8 g, 12.5 mmole) in dichloromethane (20 ml) was added and the reaction mixture was allowed to stir and warm to room temperature overnight. The reaction mixture was then washed successively with water, saturated aqueous sodium bicarbonate solution, 3N citric acid and water, dried over sodium sulphate, filtered and evaporated in vacuo to afford an oil. Column chromatography on silica eluting with a gradient of diethyl ether in hexane gave:

ISOMER A 0.36 g, (oil); (Found: [m+1]$^+$=346.2052. C$_{17}$H$_{32}$N$_2$O$_4$S requires 346.2052.); δ(CD$_3$OD) 0.9 (6H, d, J=7 HZ, CH(CH$_3$)$_2$); 1.0–1.8 (3H, m, CH$_2$CH(CH$_3$)$_2$); 1.33 (6H, d, J=8 Hz, CHCH$_3$); 1.45 (9H, s, OC(CH$_3$)$_3$); 2.29 (3H, s, SCOCH$_3$); 2.66 (1H, quintet, J-5 Hz, CH$_3$CHSCHCO); 3.75 (1H, quintet, J=5 Hz, CH$_3$CHS) and 4.25 (1H, m, α-CH). Further elution then gave

ISOMER B 0.83 g, (oil); (Found: [m+1]$^+$=346.2052. C$_{17}$H$_{32}$N$_2$O$_4$S requires 346.2052.); δ(CD$_3$OD) 0.87 (3H, d, J=7 Hz, CH(CH$_3$)$_2$); 0.89 (3H, d, J=7 Hz, CH(CH$_3$)$_2$); 1.23–1.8 (3H, m, CH$_2$CH(CH$_3$)$_2$); 1.33 (3H, d, J=8 Hz, CHCH$_3$); 1.34 (3H, d, J=8 Hz, CHCH$_3$);

1.46 (9H, s, OC(CH$_3$)$_3$); 2.32 (3H, s, SCOCH$_3$); 2.45 (1H, dt, J=8 Hz and 3 Hz, CH$_3$CHSCHCO); 3.72 (1H, m, CH$_3$CHS) and 4.28 (1H, q, J=7 and 14 Hz, α-CH).

Further elution then gave

ISOMER C 1.09 g, (solid); (Found: [m+1]$^+$ =346.2052. C$_{17}$H$_{32}$N$_2$O$_4$S requires 346.2052.); δ(CD$_3$OD) 0.92 (6H, dd, J=7 Hz, CH(CH$_3$)$_2$); 1.2–1.8 (3H, m, CH$_2$CH(CH$_3$)$_2$); 1.29 (3H, d, J=8 Hz, CHCH$_3$); 1.34 (3H, d, J=8 Hz, CHCH$_3$); 1.45 (9H, s, OC(CH$_3$)$_3$); 2.31 (3H, s, SCOCH$_3$); 2.48 (1H, m, CH$_3$CHSCHCO); 3.64 (1H, m, CH$_3$CHS) and 4.21 (1H, m, α-CH).

(b) N-[2-(1-S-Acetylmercaptoethyl)-4-methyl-pentanoyl]-L-alanine N-Butylamide

ISOMER A

The above ester (isomer A) (294 mg, 0.8 mmole) was treated with 10:1 TFA/water for 2 h. at room temperature. Volatiles were then removed in vacuo and the residue was taken up in dichloromethane and neutralised with N-methylmorpholine. After cooling to 0° 1-hydroxybenzotriazole (137 mg, 0.9 mmole) was added followed by n-butylamine (66 mg, 0.9 mmole) and N-ethyl-N'-(3-dimethylaminopropyl)carbodiimide hydrochloride (173 mg, 0.9 mmole). The reaction was then allowed to warm and stir to room temperature overnight. After dilution with dichloromethane (15 ml) the reaction mixture was washed (saturated aqueous sodium bicarbonate solution, 3N citric acid), dried and concentrated to a solid in vacuo. Recrystallisation from methanol/water gave the title compound as a white solid (47 mg), m.p. 140°–141°; (Found: C, 59.62; H, 9.63; N, 8.04. C$_{17}$H$_{32}$N$_2$O$_3$S requires C, 59.27; H, 9.36; N, 8.13%); δ(CDCl$_3$) 0.93 (9H, m, CH$_2$CH$_3$CH$_2$ (CH$_3$)$_2$); 1.2–1.84 (7H, m, CH$_2$CH(CH$_3$)$_2$, CH$_2$CH$_2$CH$_3$); 1.30 (3H, d, J-8 Hz, CHCH$_3$); 1.39 (3H, d, J=8 Hz, CHCH$_3$); 2.37 (3H, s, SCOCH$_3$); 2.55 (1H, m, CH$_3$CHSCHCO); 3.28 (2H, q, J=7 Hz, NHCH$_2$); 3.75 (1H, m, CH$_3$CHS); 4.50 (1H, m, α-CH) and 6.5–6.8 (2H, m, CONH x2).

ISOMER B

The above ester isomer B (375 mg, 1.03 mmole) was treated with 10:1 TFA/water for 2 h. at room temperature. Volatiles were then removed in vacuo and the residue was taken up in dichloromethane and neutralised with N-methylmorpholine. After cooling to 0° 1-hydroxybenzotriazole (168 mg, 1.1 mmole) was added followed by n-butylamine (80 mg, 1.1 mmole) and N-ethyl-N'-(3-dimethylaminopropyl)carbodiimide hydrochloride (211 mg, 1.1 mmole). The reaction was then allowed to warm and stir to room temperature overnight. After dilution with dichloromethane (15 ml) the reaction mixture was washed (saturated aqueous sodium bicarbonate solution, 3N citric acid), dried and concentrated to a solid in vacuo. Recrystallisation from methanol/water gave the title compound as a white solid (154 mg), m.p. 140°–141°; (Found: C, 58.98; H, 9.35; N, 7.84. C$_{17}$H$_{32}$N$_2$O$_3$S requires C, 59.27; H, 9.36; N, 8.13%); δ(CDCl$_3$) 0.91 (9H, m, CH$_2$CH$_3$, CH(CH$_3$)$_2$); 1.2–1.8 (7H, m, CH$_2$CH(CH$_3$)$_2$, CH$_2$CH$_2$CH$_3$); 1.30 (3H, d, J=8 Hz, CHCH$_3$); 1.36 (3H, d, J=8 Hz; CHCH$_3$); 2.33 (3H, s, SCOCH$_3$); 2.45 (1H, m, CH$_3$CHSCHCO); 3.26 (2H, m, NHCH$_2$); 3.70 (1H, quintet, J=7 Hz, CH$_3$CHS); 4.57 (1H, q, J=7 and 14 Hz, α-CH); 6.73 (1H, d, J=8 Hz, CONH) and 6.86 (1H, m, CONH).

ISOMER C

The above ester (isomer C) (450 mg, 1.23 mmole) was treated with 10:1 TFA/water for 2 h. at room temperature. Voltiles were then removed in vacuo and the residue was taken up in dichloromethane (10 ml) and neutralised with N-methylmorpholine. After cooling to 0° 1-hydroxybenzotriazole (199 mg, 1.3 mmole) was added followed by n-butylamine (95 mg, 1.3 mmole) and N-ethyl-N'-(3-dimethylaminopropyl)carbodiimide hydrochloride (250 mg, 1.3 mmole). The reaction was then allowed to warm and stir to room temperature overnight. After dilution with dichloromethane (15 ml) the reaction mixture was washed (saturated aqueous sodium bicarbonate solution, 3N citric acid), dried and concentrated to a solid in vacuo. Recrystallisation from methanol/water gave the title compound as a white solid (239 mg), m.p. 120°–122°; (Found: C, 59.00; H, 9.38; N, 7.74. C$_{17}$H$_{32}$N$_2$O$_3$S requires C, 59.27; H, 9.36; N, 8.13%); δ(CDCl$_3$) 0.90 (9H, m, CH$_2$CH$_3$, CH(CH$_3$)$_2$); 1.2–1.8 (7H, m, CH$_2$CH(CH$_3$)$_2$, CH$_2$CH$_2$CH$_3$); 1.33 (3H, d, J=8 Hz, CHCH$_3$); 1.39 (3H, d, J=8 Hz, CHCH$_3$); 2.34 (3H, s, SCOCH$_3$); 2.45 (1H, m, CH$_3$CHSCHCO); 3.25 (2H, m, NHCH$_2$); 3.72 (1H, quintet, J=7 Hz, CH$_3$CHS); 4.60 (1H, q, J=7 and 14 Hz, α-CH); 6.83 (1H, d, J=8 Hz, CONH) and 6.95 (1H, m, CONH).

(c) N-[2-(1-S-mercaptoethyl)-4-methyl-pentanoyl]-L-alanine N-Butylamide

ISOMER A

To a solution of the S-Acetate from above (Isomer A) (47 mg) in degassed methanol (10 ml) was added dilute aqueous ammonium hydroxide solution (2 ml). After stirring for 24 h. at room temperature the reaction mixture was concentrated in vacuo to yield a white solid (36 mg); (Found: [m+1]$^+$=303.2096. C$_{15}$H$_{30}$N$_2$O$_2$S requires 303.2106); δ(CDCl$_3$) 0.92 (9H, m, CH(CH$_3$)$_2$, CH$_2$CH$_3$); 1.22–1.83 (7H, m, CH$_2$CH(CH$_3$)$_2$, CH$_2$CH$_2$CH$_3$);; 1.39 (3H, d, J=7 Hz, CHCH$_3$); 1.40 (3H, d, J=7 Hz, CHCH$_3$); 2.24 (1H, m, CH$_3$CHSCHCO); 3.13 (1H, m, CH$_3$CHS); 3.26 (2H, q, J=7 Hz, NHCH$_2$); 4.55 (1H, m, α-CH); 6.38 (1H, d, J=8 Hz, CONH) and 6.60 (1H, m, CONH).

ISOMER B

To a solution of the S-Acetate from above (Isomer B) (119 mg) in degassed methanol (10 ml) was added dilute aqueous ammonium hydroxide solution (2 ml). After stirring for 9 h. at room temperature the reaction mixture was concentrated in vacuo to yield a white solid (75 mg); (Found; [m+1]$^+$= 303.2096. C$_{15}$H$_{30}$N$_2$O$_2$S requires 303.2106); δ(CDCl$_3$) 0.92 (9H, m, CH(CH$_3$)$_2$, CH$_2$CH$_3$); 1.24–2.00 (7H, m, CH$_2$CH(CH$_3$)$_2$, CH$_2$CH$_2$CH$_3$); 1.35 (3H, d, J=8 Hz, CHCH$_3$); 1.37 (3H, d, J=7 Hz, CHCH$_3$); 2.26 (1H, m, CH$_3$CHSCHCO); 3.08 (1H, m, CH$_3$CHS); 3.26 (2H, q, J=7 Hz, NHCH$_2$); 4.50 (1H, m, α-CH) and 6.50 (2H, m, 2×CONH).

ISOMER C

To a solution of the S-Acetate from above (Isomer C) (131 mg) in degassed methanol (10 ml) was added dilute aqueous ammonium hydroxide solution (2 ml). After stirring for 64 h. at room temperature the reaction mixture was concentrated in vacuo to yield a white solid (90 mg), m.p. 122°–125°; (Found: C, 59.36; H, 10.20; N, 9.03; S, 10.37. C$_{15}$H$_{30}$N$_2$O$_2$S requires C, 59.56; H, 10.00; N, 9.26; S, 10.60%; δ(CDCl$_3$) 0.92 (9H, m, CH(CH$_3$)$_2$, CH$_2$CH$_3$); 1.22–1.83 (7H, m, CH$_2$CH(CH$_3$)$_2$, CH$_2$CH$_2$CH$_3$); 1.38 (3H, d, J=7 Hz, CHCH$_3$); 1.41 (3H, d, J=7 Hz, CHCH$_3$); 2.22 (1H, m, CH$_3$CHSCHCO); 3.10 (1H, m, CH$_3$CHS); 3.26 (2H, q, J=7 Hz, NHCH$_2$); 4.50 (1H, m, α-CH) and 6.15–6.44 (2H, m, CONH).

Alternatively the compound isomer B1 of example 1 may be prepared by diastereoselective synthesis (E×8)

which offers only two of the potential four isomers and thereby a higher-yielding synthetic route.

EXAMPLE 8

N-[2-(1-S-Acetylmercaptoethyl)-4-methylpentanoyl]-O-methyl-L-tyrosine NMethylamide (a) N-[2-(2-methylpropyl)-but-2-enoyl]-O-methyl-L-tyrosine N-Methylamide 2-(2-Methylpropyl)-but-2-enoic acid (37 g, 0.261 M) prepared as described in Example 1 in dry dichloromethane (200 ml) and N-methyl morpholine (65 ml) was treated at −5° C. with oxalyl chloride (33.2 g, 0.261 M) over 30 minutes. The mixture was heated under reflux for 10 minutes, then re-cooled to ca −60° C. and 0-methyl-L-tyrosine N-methylamide (51 g, 0.245 M) in dry dichloromethane (100 ml) added over 30 minutes. The mixture was left to warm up to room temperature over ca 1 hour, diluted with more dichloromethane then washed with aqueous sodium hydroxide (0.1 N), aqueous saturated sodium hydrogen carbonate solution and saturated brine. The organic extract was dried, then evaporated in vacuo to afford N-[2-(2-methylpropyl)-but-2-enoyl]-O-methyl-L-tyrosine-N-methylamide as a yellow gum (81 g).

δ(CDCl$_3$) 0.84 (6H, d, J=6 Hz, (CH$_3$)$_2$CH); 1.58 (1H, m, CH(CH$_3$)$_2$); 1.74 (3H, d, J=6 Hz, CH$_3$CH); 2.19 (2H, d, J=7 Hz, CHCH$_2$C); 2.74 (3H, d, J=4 Hz, NHCH$_3$); 3.06 (2H, m, CH$_2$C$_6$H$_4$); 3.79 (3H, s, OCH$_3$); 4.60 1H, m, NHCHCO); 5.90 (1H, m, NH); 6.32 (1H, m, CH$_3$CH); 6.36 (1H, m, NH); 6.81 and 7.14 (4H, each d, each J=8 Hz, C$_6$H$_4$). Rf=0.45 in Ethyl acetate by thin layer chromatography on silica plates.

(b) N-[2-(1-S-Acetylmercaptoethyl)-4-methylpentanoyl]-O-methyl-L-tyrosine N-Methylamide The foregoing compound (80 g, 0.241 M) was stirred in the dark under an atmosphere of nitrogen with thioacetic acid (400 ml) at room temperature for 5 days. Excess acid was removed by rotary-evaporation (temperature less than 45° C.) and the residue chromatographed on silica in 20% acetonitrile in dichloromethane to afford two diastereoisomers. The faster running diastereoisomer was N-[2-(1-S-Acetylmercaptoethyl)-4-methyl-1-oxopentyl]-O-methyl-L-tyrosine N-methylamide (isomer B1) which crystallised from ethyl acetate/hexane as pale yellow needles, m.p. 85°–86° C. (Found: C, 61.08, H, 7.81, N, 6.80; C$_{21}$H$_{32}$N$_2$O$_4$S+0.2 H$_2$O requires: C, 61.20, H, 7.92, N, 6.80) which was identical with isomer B1 as described in Example 1 (by NMR and I.R. spectra).

What is claimed is:

1. A compound of the formula

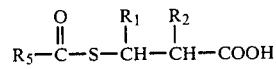

wherein R$_1$ represents lower alkyl, phenyl, or phenyl lower alkyl; R$_2$ represents lower alkyl; and R$_5$ represents lower alkyl.

* * * * *

UNITED STATES PATENT AND TRADEMARK OFFICE
CERTIFICATE OF CORRECTION

PATENT NO. : 4,681,966
DATED : July 21, 1987
INVENTOR(S) : Donald, et al.

It is certified that error appears in the above-identified patent and that said Letters Patent are hereby corrected as shown below:

Column 1, the structure to the right of the first structure, reading,

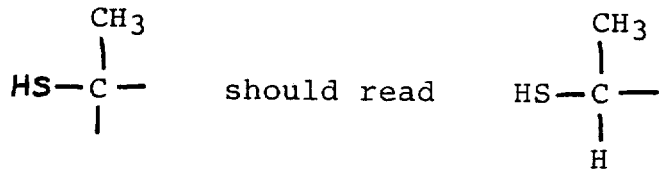

Column 9, the first structure, Table 1, that portion of the structure reading

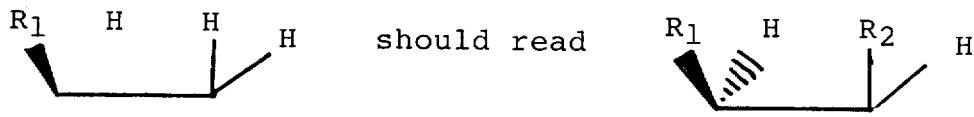

Column 14, line 47, reading "3.02(3H,m,CH$_3$);" should be deleted.

UNITED STATES PATENT AND TRADEMARK OFFICE
CERTIFICATE OF CORRECTION

PATENT NO. : 4,681,966
DATED : July 21, 1987
INVENTOR(S) : Donald, et al

It is certified that error appears in the above-identified patent and that said Letters Patent is hereby corrected as shown below:

Column 19, line 48, "6.83," should be inserted between "NH);" and "6.84," so that the portion of line 48 now reads -- "NH); 6.83, 6.84," --.

Signed and Sealed this

Twenty-second Day of November, 1988

Attest:

DONALD J. QUIGG

Attesting Officer

Commissioner of Patents and Trademarks